United States Patent
Curti et al.

(10) Patent No.: US 9,828,432 B2
(45) Date of Patent: Nov. 28, 2017

(54) CANCER TREATMENT AND MONITORING METHODS USING OX40 AGONISTS

(75) Inventors: Brendan Curti, Portland, OR (US); Magdalena Kovacsovics-Bankowski, Portland, OR (US); Ed Walker, Portland, OR (US); Josh Walker, Portland, OR (US); Andy Weinberg, Portland, OR (US)

(73) Assignee: PROVIDENCE HEALTH & SERVICES—OREGON, Renton, WA (US)

( * ) Notice: Subject to any disclaimer, the term of this patent is extended or adjusted under 35 U.S.C. 154(b) by 98 days.

(21) Appl. No.: 14/376,998

(22) PCT Filed: Feb. 6, 2012

(86) PCT No.: PCT/US2012/024009
§ 371 (c)(1),
(2), (4) Date: Dec. 8, 2014

(87) PCT Pub. No.: WO2013/119202
PCT Pub. Date: Aug. 15, 2013

(65) Prior Publication Data
US 2015/0098942 A1  Apr. 9, 2015

(51) Int. Cl.
| C07K 16/28 | (2006.01) |
| C07K 14/715 | (2006.01) |
| G01N 33/574 | (2006.01) |
| G01N 33/569 | (2006.01) |
| A61K 39/00 | (2006.01) |

(52) U.S. Cl.
CPC ...... *C07K 16/2878* (2013.01); *C07K 14/7151* (2013.01); *G01N 33/56966* (2013.01); *A61K 2039/505* (2013.01); *A61K 2039/6031* (2013.01); *C07K 2317/20* (2013.01); *C07K 2317/75* (2013.01); *C07K 2317/76* (2013.01); *C07K 2317/94* (2013.01); *C07K 2319/74* (2013.01); *G01N 2333/705* (2013.01); *G01N 2800/52* (2013.01); *G01N 2800/7028* (2013.01)

(58) Field of Classification Search
CPC ..... C07K 16/28; C07K 14/715; G01N 33/574
USPC .......................... 424/134.1, 173.1; 435/7.25
See application file for complete search history.

(56) References Cited

U.S. PATENT DOCUMENTS

| 4,683,195 A | 7/1987 | Mullis et al. |
| 5,225,539 A | 7/1993 | Winter |
| 5,639,641 A | 6/1997 | Pedersen et al. |
| 5,939,598 A | 8/1999 | Kucherlapati et al. |
| 6,312,700 B1 | 11/2001 | Weinberg |
| 7,504,101 B2 | 3/2009 | Weinberg |
| 7,622,444 B2 | 11/2009 | Weinberg |
| 7,959,925 B2 | 6/2011 | Weinberg et al. |
| 2003/0035790 A1 | 2/2003 | Chen et al. |
| 2004/0131587 A1* | 7/2004 | Thomas ............... A61K 38/191 424/85.2 |
| 2010/0028865 A1 | 2/2010 | Fazekas De St Groth et al. |
| 2011/0008368 A1 | 1/2011 | Liu et al. |
| 2015/0157710 A1 | 6/2015 | Redmond et al. |

FOREIGN PATENT DOCUMENTS

| JP | 2005206563 A | 8/2005 |
| WO | WO-9512673 A1 | 5/1995 |
| WO | WO-9521915 A1 | 8/1995 |

OTHER PUBLICATIONS

Curti et al. (Cancer Res, 2013, 73(24): 7189-98).*
Abstracts for the 25th Annual Scientific Meeting of the International Society for Biological Therapy of Cancer, Journal of Immunotherapy 33(8):859-920 (2010).
Al-Lazikani, B., et al., "Standard Conformations for the Canonical Structures of Immunoglobulins," Journal of Molecular Biology 273(4):927-948, Academic Press Limited, United States (1997).
Baum, P.R., et al., "Molecular Characterization of Murine and Human OX40/OX40 Ligand Systems: Identification of a Human OX40 Ligand as the HTLV-1-regulated Protein gp34," The EMBO Journal 13(17):3992-4001, Wiley Blackwell, England (1994).
Brahmer., J.R., et al., "Phase I Study of Single-Agent Anti-Programmed Death-1 (MDX-1106) in Refractory Solid Tumors: Safety, Clinical Activity, Pharmacodynamics, and Immunologic Correlates," Journal of Clinical Oncology 28(19):3167-3175, American Society of Clinical Oncology, United States (2010).
Calderhead, D.M., et al., "Cloning of Mouse Ox40: A T Cell Activation Marker That May Mediate T-B Cell Interactions," Journal of Immunology 151(10):5261-5271, American Association of Immunologists, United States (1993).
Campoli, M., et al., "Mechanisms of Tumor Evasion," in Tumor Immunology and Cancer Vaccines, Khleif, S.N. ed., pp. 61-88, Springer, United States (2005).
Cartilage Matrix Protein (CMP), Accession No. NP_002370, NCBI Database, accessed at http://www.ncbi.nlm.nih.gov/protein/NP_002370, Entry Date Mar. 15, 2015, Accessed on Dec. 7, 2015.
Colombo, M.P. and Piconese, S., "Regulatory-T-cell Inhibition Versus Depletion: The Right Choice in Cancer Immunotherapy," Nature Reviews Cancer 7(11):880-887, Nature Publishing Group, England (2007).
Cordone, I., et al., "Characterisation of Normal Peripheral Blood Cells in Cycle Identified by Monoclonal Antibody Ki-67," Journal of Clinical Pathology 45(3):201-205, BMJ Publishing Group, England (1992).

(Continued)

*Primary Examiner* — Yan Xiao
(74) *Attorney, Agent, or Firm* — Sterne, Kessler, Goldstein & Fox P.L.L.C.

(57) ABSTRACT

OX40 is a potent immune stimulating target. Provided herein are methods for the treatment of cancer patients using (3X40 agonists methods to predict clinical outcome of the treatment by correlation of the treatment and an increase in OX40-induced T cell proliferation.

19 Claims, 12 Drawing Sheets

(56) References Cited

OTHER PUBLICATIONS

Figure 1:
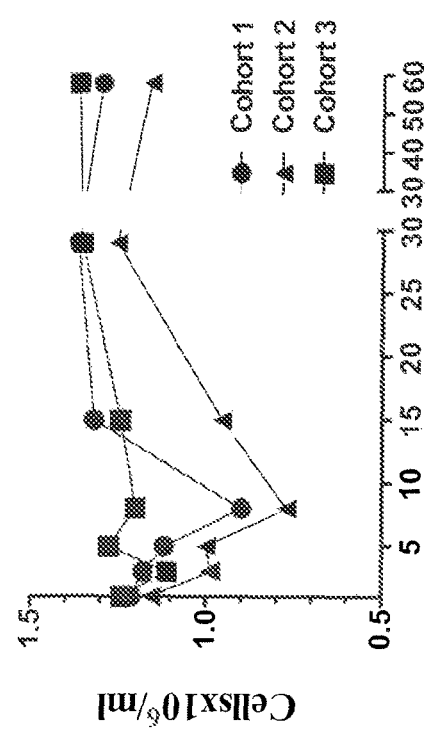

Cubilin, Accession No. NP_001072, NCBI Database, accessed at http://www.ncbi.nlm.nih.gov/protein/NP_001072, Entry Date Dec. 6, 2015, Accessed on Dec. 7, 2015.
Curran, M.A., et al., "PD-1 and CTLA-4 Combination Blockade Expands Infiltrating T Cells and Reduces Regulatory T and Myeloid Cells within B16 Melanoma Tumors," Proceedings of the National Academy of Sciences, USA 107(9):4275-4280, National Academy of Sciences, United States (2010).
Curti, B.D., et al.,"OX40 is a Potent Immune-Stimulating Target in Late-stage Cancer Patients," Cancer Research 73(24):7189-7198, American Association for Cancer Research, United States (2013).
Evans, D.E., et al., "Engagement of OX40 Enhances Antigen-Specific CD4(+) T Cell Mobilization/Memory Development and Humoral Immunity: Comparison of alphaOX-40 with alphaCTLA-4," Journal of Immunology 167(12):6804-6811, American Association of Immunologists, United States (2001).
Fong, L. and Small, E.J., "Anti-Cytotoxic T-Lymphocyte Antigen-4 Antibody: The First in an Emerging Class of Immunomodulatory Antibodies for Cancer Treatment," Journal of Clinical Oncology 26(32):5275-5283, American Society of Clinical Oncology, United States (2008).
Gattinoni, L., et al., "Adoptive Immunotherapy for Cancer: Building on Success," Nature Reviews. Immunology 6(5):383-393, Nature Publishing Group, England (2006).
Gough, M.J., et al., "OX40 Agonist Therapy Enhances CD8 Infiltration and Decreases Immune Suppression in the Tumor," Cancer Research 68(13):5206-5215, American Association for Cancer Research, United States (2008).
Gramaglia, I., et al., "The OX40 Costimulatory Receptor Determines the Development of CD4 Memory by Regulating Primary Clonal Expansion," Journal of Immunology 165(6):3043-3050, American Association of Immunologists, United States (2000).
Heat Shock Transcription Factor 1 (HSF1), Accession No. AAX42211, NCBI Database, accessed at http://www.ncbi.nlm.nih.gov/protein/AAX42211, Entry Date Mar. 29, 2015, Accessed on Dec. 7, 2015.
Hiraoka, N., "Tumor-infiltrating Lymphocytes and Hepatocellular Carcinoma: Molecular Biology," International Journal of Clinical Oncology 15(6):544-551, Springer-Verlag Tokyo, Japan (2010).
International Search Report for International Application No. PCT/US2012/024009, United States Patent and Trademark Office, United States, dated May 23, 2012, 3 pages.
Jones, P.T., et al., "Replacing the Complementarity-Determining Regions in a Human Antibody with those from a Mouse," Nature 321(6069):522-525, Nature Publishing Group, England (1986).
Kavanagh, B., et al., "CTLA4 Blockade Expands FoxP3+ Regulatory and Activated Effector CD4+ T Cells in a Dose-dependent fashion," Blood 112(4):1175-1183, American Society of Hematology, United States (2008).
Kjaergaard, J., et al., "Therapeutic Efficacy of OX-40 Receptor Antibody Depends on Tumor Immunogenicity and Anatomic Site of Tumor Growth," Cancer Research 60(19):5514-5521, American Association for Cancer Research, United States (2000).
Lee, S.W., et al., "Functional Dichotomy Between OX40 and 4-1BB in Modulating Effector CD8 T Cell Responses," Journal of Immunology 177(7):4464-4472, American Association of Immunologists, United States (2006).
Ma, B.Y., et al., "The Expression and the Regulatory Role of OX40 and 4-1BB Heterodimer in Activated Human T Cells," Blood, 106(6):2002-2010, American Society of Hematology, United States (2005).
Mallett, S., et al., "Characterization of the MRC Ox40 Antigen of Activated CD4 Positive T Lymphocytes—A Molecule Related to Nerve Growth Factor Receptor," The EMBO Journal 9(4):1063-1068, Wiley Blackwell, England (1990).
Matrilin-4, Accession No. O95460, NCBI Database, accessed at http://www.ncbi.nlm.nih.gov/protein/O95460, Entry Date Nov. 11, 2015, Accessed on Dec. 7, 2015.

Maxwell, J.R., et al., "Danger and OX40 Receptor Signaling Synergize to Enhance Memory T Cell Survival by Inhibiting Peripheral Deletion," Journal of Immunology 164(1):107-112, American Association of Immunologists, United States (2000).
Melero, I., et al., "Immunostimulatory Monoclonal Antibodies for Cancer Therapy," Nature Reviews. Cancer 7(2):95-106, Nature Publishing Group, England (2007).
Miller, J.D., et al., "Human Effector and Memory CD8+ T cell Responses to Smallpox and Yellow Fever Vaccines," Immunity 28(5):710-722, Cell Press, United States (2008).
Morris, N.P., et al., "Development and Characterization of Recombinant Human Fc:OX40L Fusion Protein Linked via a Coiled-coil Trimerization Domain," Molecular Immunology 44(12):3112-3121, Pergamon Press, England (2007).
Oken, M.M., et al., "Toxicity and Response Criteria of the Eastern Cooperative Oncology Group," American Journal of Clinical Oncology 5(6):649-655, Lippincott Williams & Wilkins, United States (1982).
Pardee, A.D., et al., "A Therapeutic OX40 Agonist Dynamically Alters Dendritic, Endothelial, and T Cell Subsets within the Established Tumor Microenvironment," Cancer Research 70(22):9041-9052, American Association for Cancer Research, United States (2010).
Paterson, D.J., et al., "Antigens of Activated Rat T Lymphocytes Including a Molecule of 50,000 M Detected Only on CD4 Positive T Blasts," Molecular Immunology 24(12):1281-1290, Pergamon Press, England (1987).
Peggs, K.S., et al., "Blockade of CTLA-4 on Both Effector and Regulatory T Cell Compartments Contributes to the Antitumor Activity of Anti-CTLA-4 Antibodies," The Journal of Experimental Medicine 206(8):1717-1725, Rockefeller University Press, United States (2009).
Piconese, S., et al., "OX40 Triggering Blocks Suppression by Regulatory T Cells and Facilitates Tumor Rejection," The Journal of Experimental Medicine 205(4):825-839, Rockefeller University Press, United States (2008).
Pitcher, C.J., et al., "Development and Homeostasis of T Cell Memory in Rhesus Macaque," Journal of Immunology 168(1):29-43,American Association of Immunologists, United States (2002).
Riechmann, L., et al., "Reshaping Human Antibodies for Therapy," Nature 332(6162):323-327, Nature Publishing Group, United States (1988).
Rodriguez, P.C. and Ochoa, A.C., "Arginine Regulation by Myeloid Derived Suppressor Cells and Tolerance in Cancer: Mechanisms and Therapeutic Perspectives," Immunological Reviews 222:180-191, Blackwell, England (2008).
Rubio, J., et al., "Immunohistochemical Expression of Ki-67 Antigen, Cox-2 and Bax/Bcl-2 in Prostate Cancer; Prognostic Value in Biopsies and Radical Prostatectomy Specimens," European Urology 48(5):745-751, Elsevier Science, Switzerland (2005).
Ruby, C.E. and Weinberg, A.D., "The effect of aging on OX40 agonist-mediated cancer immunotherapy," Cancer Immunology Immunotherapy 58(12):1941-1947, Springer Verlag, Germany (2009).
Ruby, C.E., et al., "Cutting Edge: OX40 Agonists Can Drive Regulatory T Cell Expansion if the Cytokine Milieu Is Right," The Journal of Immunology 183(8):4853-4857, American Association of Immunologists, United States (2009).
Supplementary European Search Report for European Application No. 12 86 8058, European Patent Office, Netherlands, dated Jul. 22, 2015, 2 pages.
Thrombospondin-1, Accession No. P07996, NCBI Database, accessed at http://www.ncbi.nlm.nih.gov/protein/P07996, Entry Date Nov. 11, 2015, Accessed on Dec. 7, 2015.
TRAF2, Accession No. Q12933, NCBI Database, accessed at http://www.ncbi.nlm.nih.gov/protein/Q12933, Entry Date Nov. 11, 2015, Accessed on Dec. 7, 2015.
Verhoeyen, M., et al., "Reshaping Human Antibodies: Grafting an Antilysozyme Activity," Science 239(4847):1534-1536, American Association for the Advancement of Science, United States (1988).

(56) References Cited

OTHER PUBLICATIONS

Weinberg, A.D., et al., "Anti-OX40 (CD134) Administration to Nonhuman Primates: Immunostimulatory Effects and Toxicokinetic Study," Journal of Immunotherapy 29(6):575-585, Wiley Blackwell, England (2006).

Weinberg, A.D., et al., "Science Gone Translational: the OX40 Agonist Story," Immunological Reviews 244(1):218-231, Blackwell, England (Nov. 2011).

Weinberg, A.D., et al., "Engagement of the OX-40 Receptor in Vivo Enhances Antitumor Immunity," Journal of Immunology 164(4):2160-2169, American Association of Immunologists, United States (2000).

Lee, S.J., et al., "4-1BB and OX40 Dual Costimulation Synergistically Stimulate Primary Specific CD8 T Cells for Robust Effector Function," Journal of Immunology 173(5):3002-3012, American Association of Immunologists, United States (2004).

Croft, M., "Control of Immunity by the TNFR-related Molecule OX40 (CD134)," Annual Review of Immunology 28:57-78, Annual Reviews Incorporation, United States (2010).

Croft, M., "Co-stimulatory Members of the TNFR Family: Keys to Effective T-cell Immunity?," Nature Reviews. Immunology 3(8):609-620, Nature Publishing Group, England (2003).

Gramaglia, I., et al., "Ox-40 Ligand: A Potent Costimulatory Molecule for Sustaining Primary CD4 T Cell Responses," Journal of Immunology 161(12):6510-6517, American Association of Immunologists, United States (1998).

International Search Report for International Application No. PCT/US12/27496, United States Patent and Trademark Office, United States, dated Jun. 8, 2012, 3 pages.

Lathrop, S.K., et al., "A Signal through OX40 (CD134) Allows Anergic, Autoreactive T Cells to Acquire Effector Cell Functions," Journal of Immunology 172(11):6735-6743, American Association of Immunologists, United States (2004).

Redmond, W.L. and Weinberg, A.D., "Targeting OX40 and OX40L for the Treatment of Autoimmunity and Cancer," Critical Reviews in Immunology 27(5):415-436, Begell House, United States (2007).

Redmond, W.L., et al., "Defects in the Acquisition of CD8 T Cell Effector Function after Priming with Tumor or Soluble Antigen can be Overcome by the Addition of an OX40 Agonist," Journal of Immunology 179(11):7244-7253, American Association of Immunologists, United States (2007).

Redmond, W.L., et al., "Ligation of the OX40 co-stimulatory Receptor Reverses Self-Ag and Tumor-induced CD8 T-cell Energy in Vivo," European Journal of Immunology 39(8):2184-2194, Wiley-VCH, Germany (2009).

Watts, T.H., "TNF/TNFR Family Members in Costimulation of T Cell Responses," Annual Review of Immunology 23:23-68, Annual Reviews Incorporation, United States (2005).

Kjaergaard, J., et al., "Augmentation Versus Inhibition: Effects of Conjunctional OX-40 Receptor Monoclonal Antibody and IL-2 Treatment on Adoptive Immunotherapy of Advanced Tumor," J Immunol 167:6669-6677, American Association of Immunologists, United States (2001).

Marzo, A.L., et al., "Tumor Antigens are Constitutively Presented in the Draining Lymph Nodes," J Immunol 162:5835-5845, American Association of Immunologists, United States (1999).

Office Action dated Feb. 23, 2017, in U.S. Appl. No. 14/381,785, Redmond, W., et al., filed Dec. 31, 2014.

Redmond, W.L., et al., "The role of OX40-mediated co-stimulation in T cell activation and survival," Cri Rev Immunol 29(3):187-201, CRC Press, United States (2009).

Safar, M. and Junghans, R.P., "Interleukin 2 maintains biologic stability and sterility over prolonged time," Immunopharmacology 29:419-423, Elsevier Science B.V., Netherlands (2000).

Trickett, A. and Kwam, Y.L., "T cell stimulation and expansion using anti-CD3/CD28 beads," Journal of Immunological Methods 275:251-255, Elsevier B.V., Netherlands (2003).

* cited by examiner

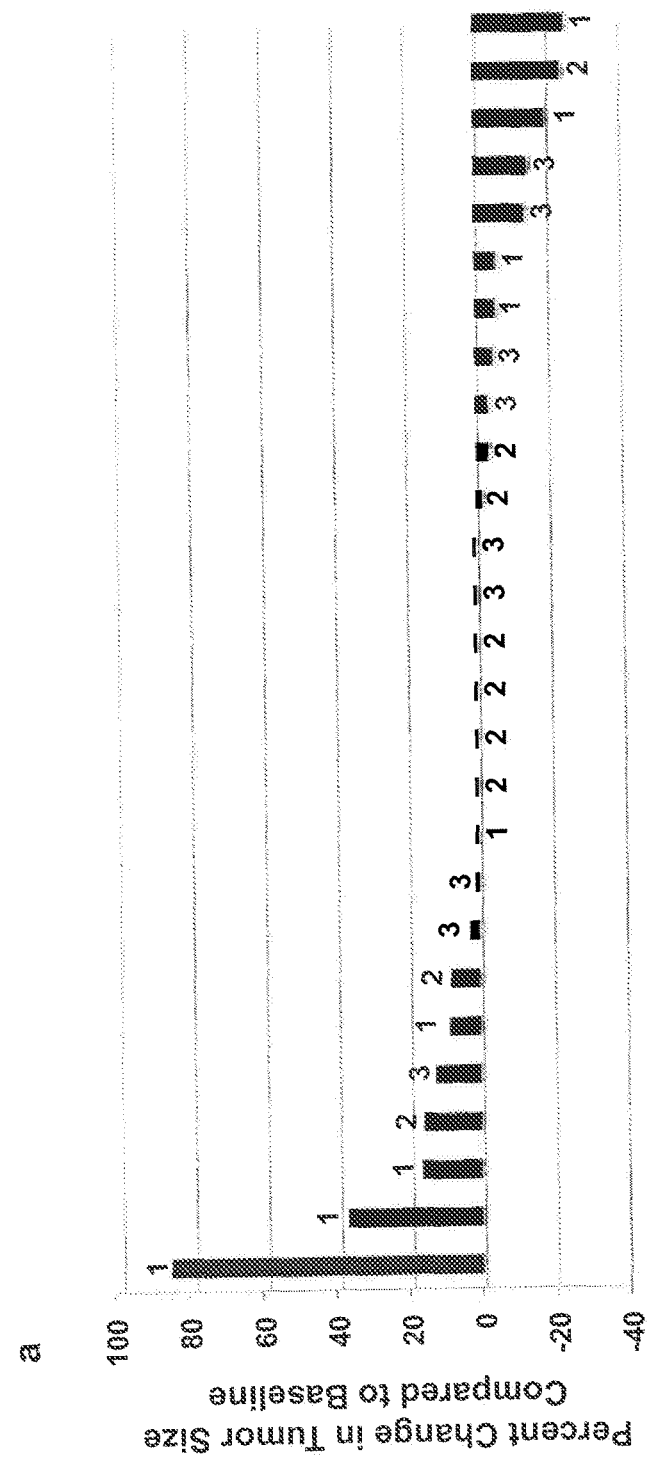

CANCER TREATMENT AND MONITORING METHODS USING OX40 AGONISTS

BACKGROUND

It is well documented that peripheral T cells from patients with metastatic cancer exhibit functional defects, including a diminished capacity to proliferate (Campoli, M., et al. *Cancer Treat Res* 123, 61-88 (2005); Gattinoni, L., et al. *Nat Rev Immunol* 6, 383-393 (2006); Rodriguez, P. C. & Ochoa, A. C. *Immunol Rev* 222, 180-191 (2008)). This loss of T cell function is likely a major factor in the failure of a host to mount an effective immune response to its own tumor. Tumor-reactive T cells are present in patients with cancer, but they are therapeutically ineffective as evidenced by tumor growth within these hosts (Hiraoka, N. *Int J Clin Oncol* 15, 544-551 (2010)). However, these same T cells recover functionally if they are removed from the suppressive tumor microenvironment, expanded to large numbers in vitro, and transferred back to the tumor-bearing hosts. This form of adoptive immunotherapy has been particularly effective leading to durable clinical responses in melanoma patients (Gattinoni, L., et al. *Nat Rev Immunol* 6, 383-393 (2006)). Thus, there is a need to restore function to dysfunctional tumor-reactive T cells in cancer immunotherapy research.

Antibodies that target certain T cell surface proteins have been shown to restore/enhance the function of tumor-reactive T cells in vivo in tumor-bearing hosts-anti-CTLA-4, anti-PD-1, anti-4-1BB, and anti-OX40 (Melero, I., et al. *Nat Rev Cancer* 7, 95-106 (2007); Fong, L. & Small, E. J. *J Clin Oncol* 26, 5275-5283 (2008); Peggs, K. S., et al. *J Exp Med* 206, 1717-1725 (2009); Curran, M. A., et al. *Proc Natl Acad Sci USA* 107, 4275-4280 (2010); Brahmer, J. R., et al. *J Clin Oncol* 28, 3167-3175 (2010)). These antibodies, alone or in combination, are being investigated as to whether they can restore T cell function in cancer patients. They could be more practical than adoptive T cell therapy because of their ease of administration and their potential value for patients with many different types of malignancies.

OX40 is a TNF-receptor family member that is expressed primarily on activated $CD4^+$ and $CD8^+$ T cells (Paterson, D. J., et al. *Mol Immunol* 24, 1281-1290 (1987); Mallett, S., et al. *EMBO J* 9, 1063-1068 (1990); Calderhead, D. M., et al. *J Immunol* 151, 5261-5271 (1993)). Preclinical cancer models have shown that OX40 agonists have potent anti-tumor activity against multiple tumor types, which is dependent on both $CD4^+$ and $CD8^+$ T cells (Kjaergaard, J., et al. *Cancer Res* 60, 5514-5521 (2000); Weinberg, A. D., et al. *J Immunol* 164, 2160-2169 (2000); Gough, M. J., et al. *Cancer Res* 68, 5206-5215 (2008); Piconese, S., Valzasina, B. & Colombo, M. P. *J Exp Med* 205, 825-839 (2008)). Immunization models have shown that OX40 agonists enhanced T cell proliferation, effector cytokine production, cytotoxicity, and decreased activation-induced cell death and increased the generation of memory T cells in non-human model systems (Gramaglia, I., et al. *J Immunol* 165, 3043-3050. (2000); Maxwell, J. R., et al. *J Immunol* 164, 107-112 (2000); Lee, S. W., et al. *J Immunol* 177, 4464-4472 (2006); Ruby, C. E. & Weinberg, A. D. *Cancer Immunol Immunother* 58, 1941-1947 (2009)). There remains a need to develop methods for stimulating the immune system of human cancer patients, and to determine whether the immune-enhancement treatment is effective.

BRIEF SUMMARY

In certain aspects, methods of treating cancer are provided.

In certain aspects the method of treating cancer includes administering to a patient in need of treatment an effective amount of an OX40 agonist, wherein the administration increases the level of Ki-67 expression in T-lymphocytes of the patient, or a subpopulation thereof over a corresponding baseline level, and can stimulate T-lymphocyte activity against cancer cells in the patient.

In certain aspects the method of treating cancer includes: (a) administering to a patient in need of treatment an effective amount of an OX40 agonist; and (b) detecting the level of Ki-67 expression in the patient's T-lymphocytes, or a subpopulation thereof, obtained at one or more time points following the administration; wherein the administration can stimulate T-lymphocyte activity against the cancer cells in the patient; and wherein an increase in the Ki-67 expression level in the patient's T-lymphocytes or subpopulation thereof compared to a corresponding baseline level is prognostic of effective treatment.

In certain aspects the method of treating cancer includes: (a) administering to a patient in need of treatment an effective amount of an OX40 agonist; (b) obtaining T-lymphocytes from the patient at one or more time points following the administration; and (c) submitting the T-lymphocytes for detection of the level of Ki-67 expression in the T-lymphocytes or a subpopulation thereof and comparison to a corresponding baseline level of Ki-67 expression; wherein the administration can stimulate T-lymphocyte activity against the cancer cells in the patient; and wherein an increase in Ki-67 expression in the patient's T-lymphocytes or subpopulation thereof over baseline following the administration is prognostic of effective treatment.

In certain aspects the method of treating cancer includes: (a) administering to a patient in need of treatment an effective amount of an OX40 agonist; (b) obtaining T-lymphocytes from the patient at one or more time points following the administration; (c) detecting the level of Ki-67 expression in the T-lymphocytes or a subpopulation thereof and comparison to a corresponding baseline level of Ki-67 expression; and (d) comparing the Ki-67 expression level to a corresponding baseline level; wherein the administration can stimulate T-lymphocyte activity against the cancer cells in the patient; and wherein an increase in Ki-67 expression in the patient's T-lymphocytes or subpopulation thereof over baseline following the administration is prognostic of effective treatment.

In certain aspects, this disclosure provides methods of monitoring whether a cancer patient will respond to treatment with the OX40 agonist.

Certain aspects provide a method of monitoring whether a cancer patient who has been administered an OX40 agonist will respond to treatment with the OX40 agonist includes: (a) detecting the level of Ki-67 expression in the patient's T-lymphocytes, or a subpopulation thereof, obtained from the patient at one or more time points following administration of the OX40 agonist; and (b) comparing the level of Ki-67 expression obtained in (a) to a corresponding baseline level of Ki-67 expression, wherein an increase over baseline in the level of Ki-67 expression in the T-lymphocytes or subpopulation thereof obtained following administration of the OX40 agonist identifies a patient who will respond to treatment with an OX40 agonist.

In certain aspects the method of monitoring whether a cancer patient will respond to treatment with the OX40 agonist includes: (a) administering to a cancer patient an effective amount of an OX40 agonist; (b) detecting the level of Ki-67 expression in the patient's T-lymphocytes, or a subpopulation thereof, obtained from the patient at one or more time points following administration of the OX40 agonist; and (c) comparing the level of Ki-67 expression obtained in (b) to a corresponding baseline level of Ki-67 expression, wherein an increase over baseline in the level of Ki-67 expression in the T-lymphocytes or subpopulation thereof obtained following administration of the OX40 agonist identifies a patient who will respond to treatment with an OX40 agonist.

In certain aspects the method of monitoring whether a cancer patient will respond to treatment with the OX40 agonist includes: (a) instructing a healthcare professional to administer an effective amount of an OX40 agonist to a cancer patient in need thereof; (b) detecting the level of Ki-67 expression in the patient's T-lymphocytes, or a subpopulation thereof, obtained from the patient at one or more time points following administration of the OX40 agonist; and (c) comparing the level of Ki-67 expression obtained in (b) to a corresponding baseline level of Ki-67, wherein an increase over baseline in the level of Ki-67 expression in the T-lymphocytes or subpopulation thereof obtained following administration of the OX40 agonist identifies a patient who will respond to treatment with an OX40 agonist.

In certain aspects the method of monitoring whether a cancer patient will respond to treatment with the OX40 agonist includes: (a) administering to a cancer patient an effective amount of an OX40 agonist; (b) obtaining T-lymphocytes from the patient at one or more time points following the administration; and (c) submitting the T-lymphocytes for detection of the level of Ki-67 expression in the T-lymphocytes or a subpopulation thereof and comparison to a corresponding baseline level of Ki-67 expression; wherein an increase over baseline in the level of Ki-67 expression in the T-lymphocytes or subpopulation thereof obtained following administration of the OX40 agonist identifies a patient who will respond to treatment with an OX40 agonist.

In certain aspects of the treatment or monitoring methods provided herein the corresponding baseline level of Ki-67 expression is established by averaging the Ki-67 expression level in T-lymphocytes or the same subpopulation thereof, obtained from a population of donors, e.g., normal healthy donors or donors who are cancer patients.

In certain aspects of the treatment or monitoring methods provided herein the corresponding baseline level of Ki-67 expression is the Ki-67 expression level in T-lymphocytes, or the same subpopulation thereof obtained from the patient prior to administration of the OX40 agonist.

In certain aspects of the treatment or monitoring methods provided herein the subpopulation of T-lymphocytes can be effector T-lymphocytes.

In certain aspects of the treatment or monitoring methods provided herein the subpopulation of T-lymphocytes can be CD4$^+$ Foxp3$^-$ T-lymphocytes. In certain aspects where the subpopulation of T-lymphocytes is CD4+ Foxp3$^-$ T-lymphocytes, the increase in the level of Ki-67 expression in the CD4$^+$ Foxp3$^-$ T-lymphocytes can be detected at a time point of less than about one week from the OX40 agonist administration.

In certain aspects of the treatment or monitoring methods provided herein the subpopulation of T-lymphocytes can be CD8$^+$ T-lymphocytes. In certain aspects where the subpopulation of T-lymphocytes is CD8$^+$ T-lymphocytes, the increase in the level of Ki-67 expression in the CD8$^+$ T-lymphocytes is first detected at a time point of at least about one week from the OX40 agonist administration. In certain aspects where the subpopulation of T-lymphocytes is CD8$^+$ T-lymphocytes, the administration of an OX40 agonist additionally increases the proportion of T-lymphocytes expressing CD38, HLA-DR expression, or both CD38 and HLA-DR.

In certain aspects of the treatment or monitoring methods provided herein an increase in Ki-67 expression is not detected in CD4$^+$ FoxP3$^+$ T-lymphocytes.

In certain aspects of the treatment or monitoring methods provided herein the increase in Ki-67 expression in the patient's T-lymphocytes, or subpopulation thereof, can be at least about 0.5-fold or at least about two-fold relative to the corresponding baseline level.

In certain aspects of the treatment or monitoring methods provided herein an increase in the level of Ki-67 expression is detected in a subpopulation of T-lymphocytes which respond to a tumor-specific antigen.

In certain aspects of the treatment or monitoring methods provided herein an increase in the level of Ki-67 expression is detected in memory T-lymphocytes.

In certain aspects of the treatment or monitoring methods provided herein the OX40 agonist is a binding molecule which specifically binds to OX40.

In certain aspects the binding molecule includes an antibody which specifically binds to OX40, or an antigen-binding fragment thereof, e.g., a monoclonal antibody, a chimeric antibody, a humanized antibody, or a human antibody. In certain aspects the antigen-binding fragment is an Fab fragment, an Fab' fragment, an F(ab)2 fragment, a single-chain Fv fragment, or a single chain antibody. In certain aspects the antibody which specifically binds to OX40, or an antigen-binding fragment thereof binds to the same OX40 epitope as mAb 9B12.

In certain aspects the binding molecule includes an OX40 ligand or OX40-binding fragment thereof.

In certain aspects the binding molecule further includes a heterologous polypeptide fused thereto. In certain aspects the binding molecule is conjugated to an agent selected from the group consisting of a therapeutic agent, a prodrug, a peptide, a protein, an enzyme, a virus, a lipid, a biological response modifier, a pharmaceutical agent, or PEG.

In certain aspects the binding molecule includes a fusion polypeptide comprising in an N-terminal to C-terminal direction: an immunoglobulin domain, wherein the immunoglobulin domain includes an Fc domain; a trimerization domain, wherein the trimerization domain includes a coiled coil trimerization domain; and a receptor binding domain, wherein the receptor binding domain is an OX40 receptor binding domain, and wherein the fusion polypeptide self-assembles into a trimeric fusion protein. In certain aspects this fusion polypeptide is capable of binding to the OX40 receptor and stimulating at least one OX40 mediated activity. In certain aspects this the OX40 receptor binding domain of this fusion polypeptide includes an extracellular domain of OX40 ligand (OX40L). In certain aspects the trimerization domain of this fusion protein includes a TRAF2 trimerization domain, a Matrilin-4 trimerization domain, or a combination thereof.

In certain aspects of the treatment or monitoring methods provided herein the cancer is a solid tumor, or a metastasis thereof. In certain aspects of the treatment or monitoring methods provided herein the cancer is, for example, melanoma, gastrointestinal cancer, renal cell carcinoma, prostate cancer, lung cancer, or any combination thereof. In certain aspects of the treatment or monitoring methods provided herein where the cancer has metastasized, a metastasis can be sited in lymph node, lung, liver, bone, or any combination thereof.

In certain aspects of the treatment methods provided herein the treatment further includes administering to the patient at least one additional cancer treatment. The additional cancer treatment can be, for example, surgery, radiation, chemotherapy, immunotherapy, targeting anti-cancer therapy, hormone therapy, or any combination thereof.

In certain aspects of the treatment or monitoring methods provided herein the OX40 agonist is administered as a single dose. In certain aspects of the treatment or monitoring methods provided herein the OX40 agonist is administered in at least two doses. In certain aspects of the treatment or monitoring methods provided herein the OX40 agonist is administered by IV infusion.

In certain aspects of the treatment or monitoring methods provided herein the level of Ki-67 expression in T-lymphocytes can be detected by flow cytometry of peripheral blood mononuclear cells (PBMCs). In certain aspects, the PBMCs can be analyzed by flow cytometry for expression of the CD3, CD95, and CD4 markers. In certain aspects PBMCs expressing the CD3, CD95, and CD4 markers can be further analyzed by flow cytometry for expression of the FoxP3 marker. In certain aspects, the PBMCs can analyzed by flow cytometry for expression of the CD3, CD95, and CD8 markers. In certain aspects PBMCs expressing the CD3, CD95, and CD8 markers can be further analyzed by flow cytometry for expression of the CD28 marker. In certain aspects PBMCs expressing the CD3, CD95, and CD8 markers can be further analyzed by flow cytometry for expression of the CD38 marker, the HLA-DR marker, or the CD38 and HLA-DR markers.

In certain aspects of the treatment or monitoring methods provided herein the patient is a human patient.

In certain aspects of the treatment methods provided herein the treatment results in a regression of at least one tumor or metastasis in the patient. In certain aspects of the treatment methods provided herein the treatment results in retarded or no increase in tumor or metastatic growth in the patient. In certain aspects of the treatment methods provided herein the treatment results in stabilization of disease in the patient.

BRIEF DESCRIPTION OF THE DRAWINGS/FIGURES

FIG. 1: Total peripheral lymphocyte counts following administration of the 9B12 anti-OX40 monoclonal antibody. Absolute lymphocyte count was analyzed in all patients. Results are presented as mean values for each cohort.

Figure 2:
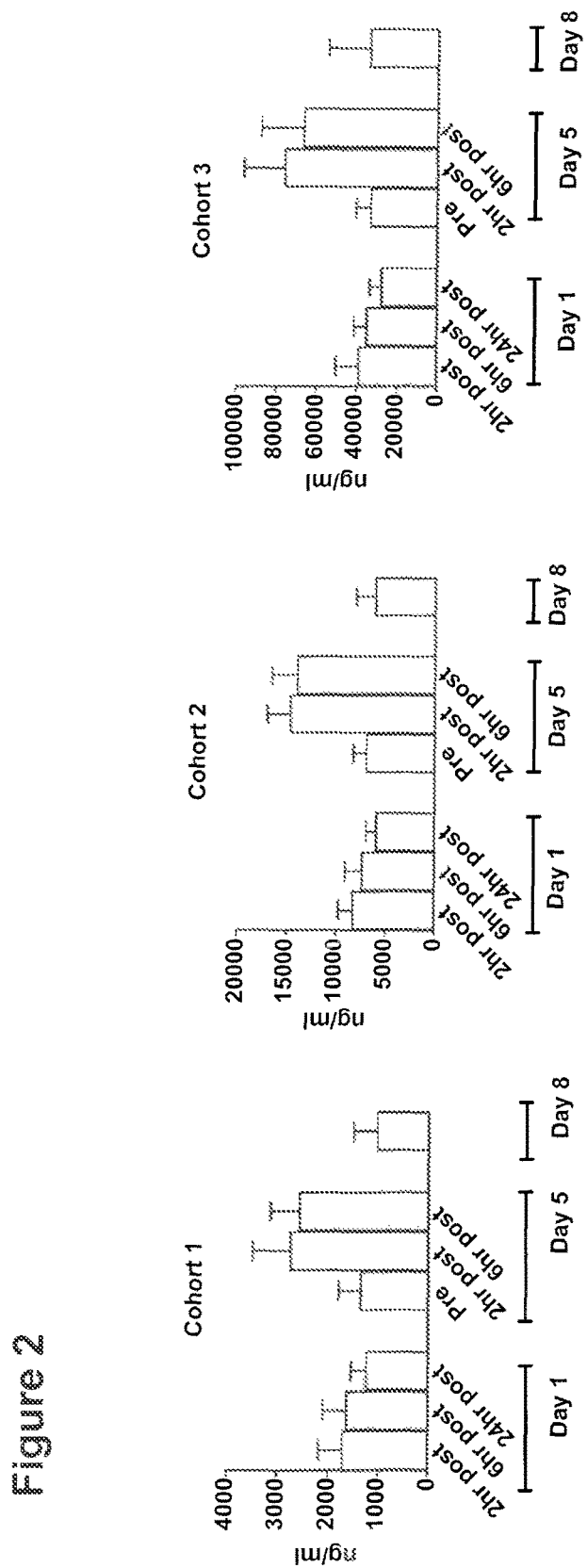

FIG. 2: Pharmacokinetics of the 9B12 anti-OX40 monoclonal antibody in patients. Patients were infused with anti-OX40 mAb on days 1, 3 and 5. Blood samples were taken before (pre), and 2, 6 and 24 hours after the day 1 dose and before (D5-pre), 2 and 6 hours after the day 5 dose. The last sample was obtained on day 8. Each point represents the mean value for the ten patients at that time point. The concentration of the 9B12 anti-OX40 monoclonal antibody was determined by ELISA as described in the Examples.

Figure 3:
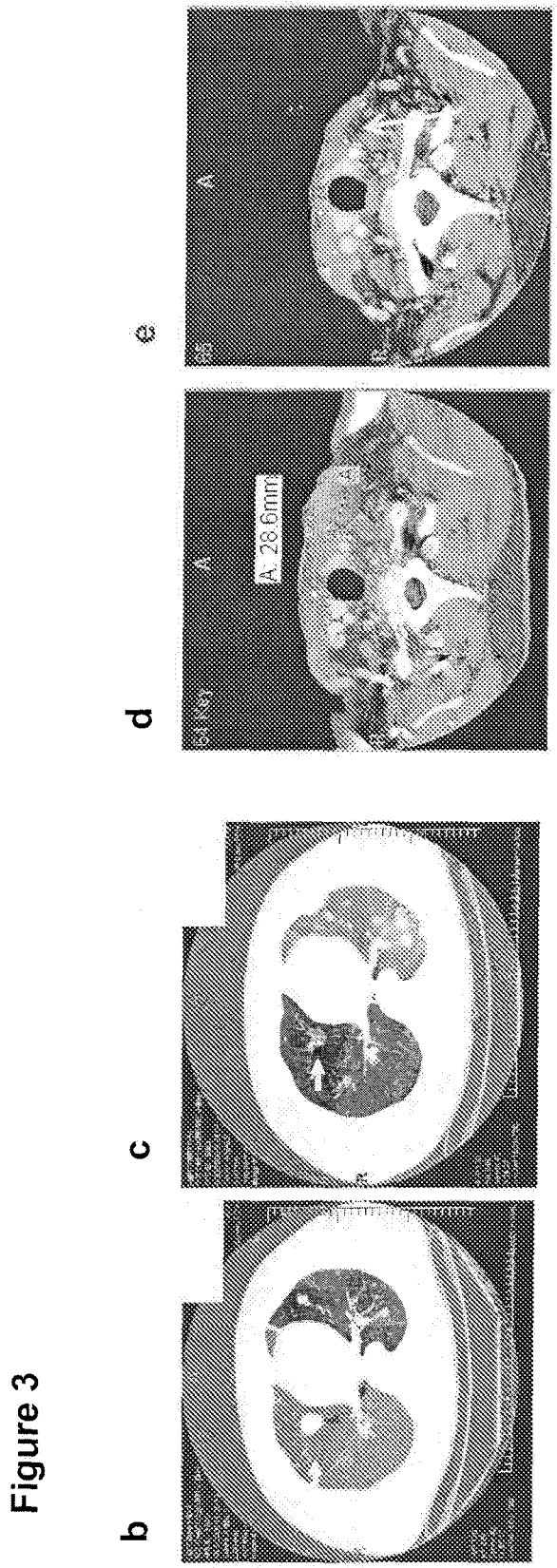
Figure 3:
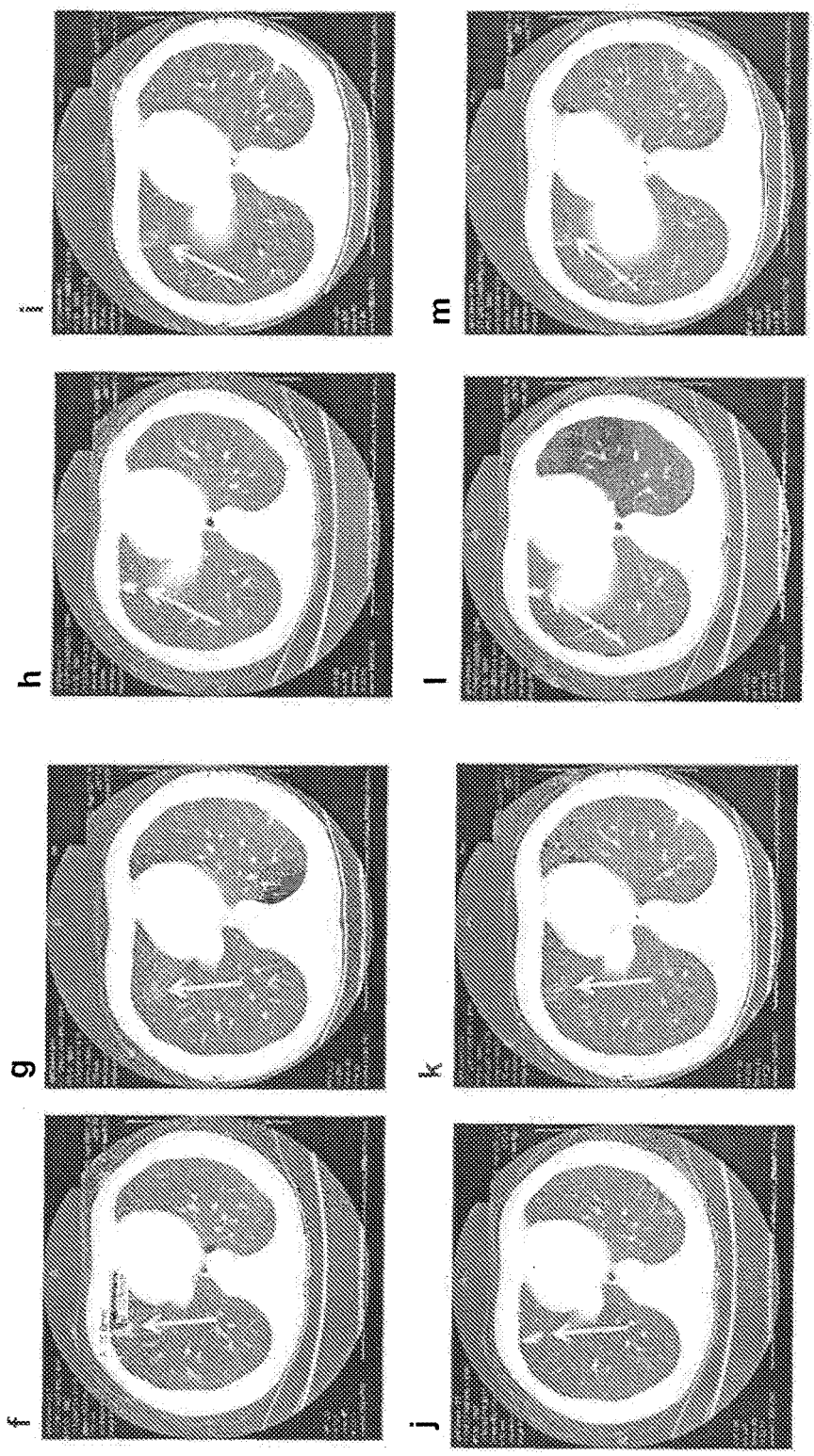

FIG. 3: Clinical responses. (a) Waterfall plot of best tumor response for patients with a least one follow-up scan expressed as percent change from baseline using Response Evaluation Criteria in Solid Tumors (RECIST) criteria. The bars are numbered according to the cohorts of patients enrolled in the study, cohort 1 (0.1 mg/kg), cohort 2 (0.4 mg/kg) and cohort 3 (2 mg/kg). Patients 10, 18 and 23 did not have follow-up scans due to clinical progression and are PD (suffering from progressive disease). (b-c) Regression of a pulmonary nodule in a patient (Cohort 1 with metastatic melanoma, and progression of other nodules. The image in panel b was obtained before administration of the 9B12 anti-OX40 monoclonal antibody. Imaging in panel c was obtained 5 months after administration. (d-e) Shrinkage of a lymph node in a patient with melanoma treated in cohort 3. (f-m) Regression of a pulmonary metastasis in a patient with renal carcinoma enrolled in cohort 1. The CT-scans were taken prior to and 2 months after the infusion of anti-OX40 the monoclonal Ab. Four serial sections are shown prior to (f, h, j, l) and after (g, i, k, m) anti-OX40 treatment in order to reaffirm that the lesion completely regressed.

Figure 4:
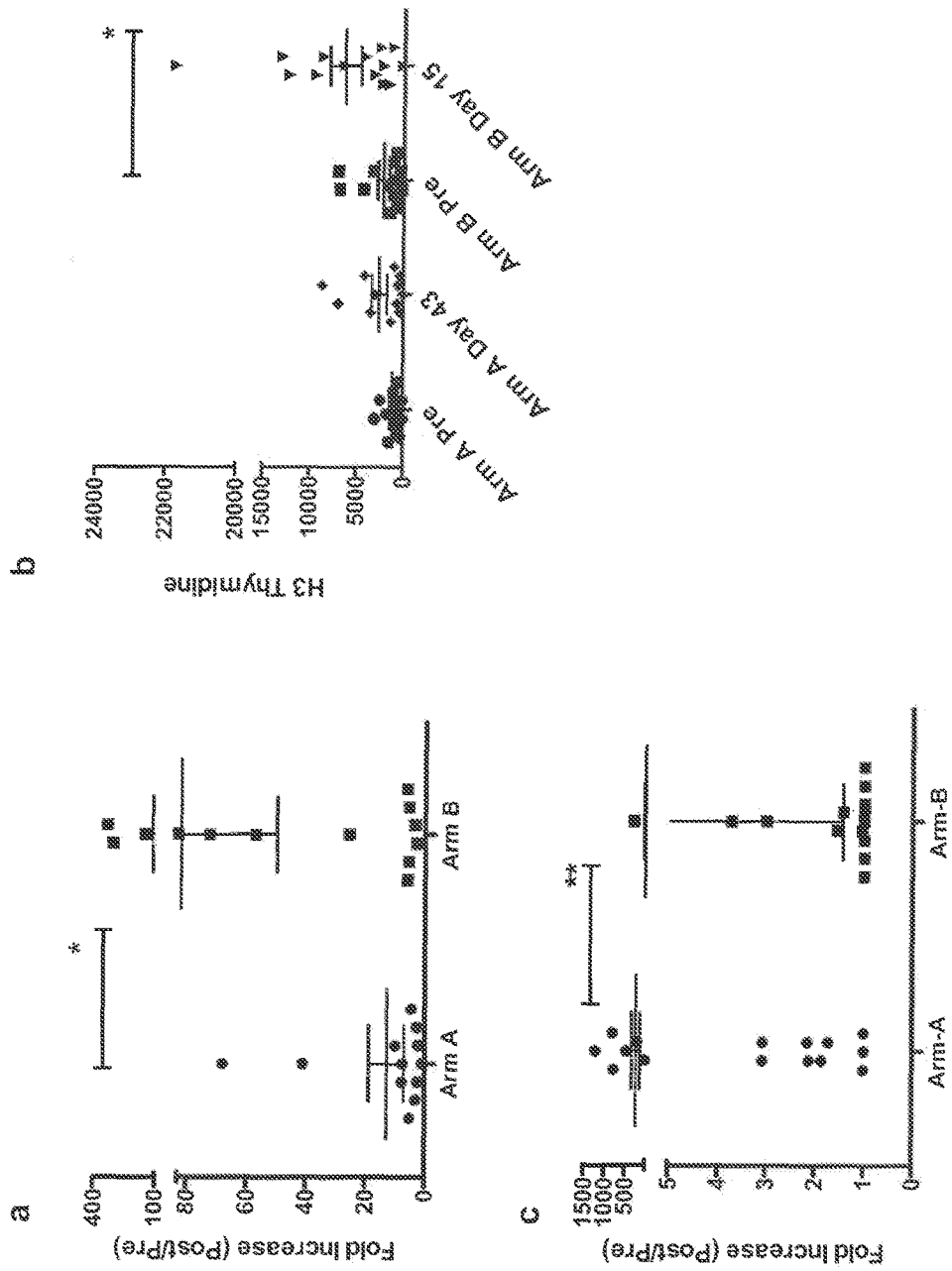

FIG. 4: (a) anti-tetanus, and (c) anti-KHL antibody titer fold increase as measured by ELISA on Day 15 and 43 (15 days after vaccination), as explained in Example 3. Increase in antibody titer was compared to samples obtained prior to the administration of the 9B12 anti-OX40 monoclonal antibody. (b) Tetanus-specific T cell proliferation was measured on Day 43 for Arm A and Day 15 for Arm B, respectively 15 days after vaccination. * p<0.05, ** p<0.001.

Figure 5:
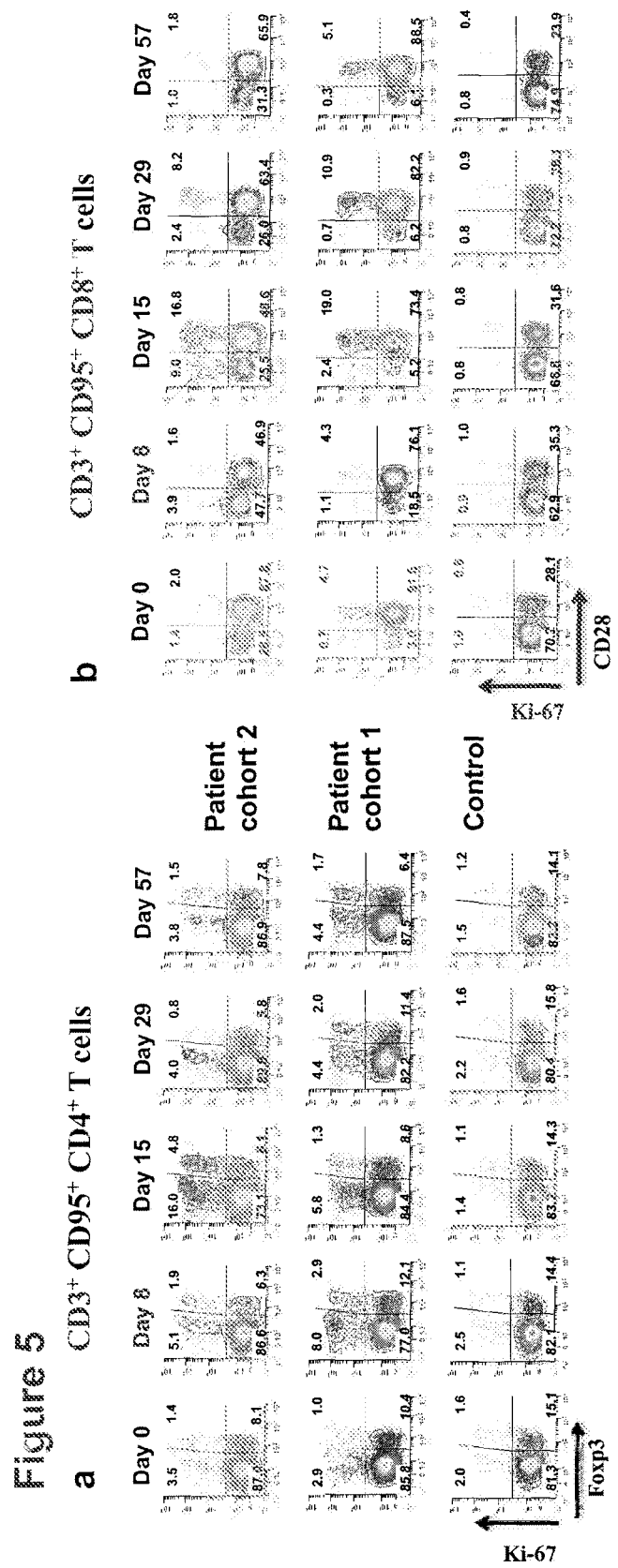

FIG. 5: Changes in Ki-67 expression within $CD4^+$ and $CD8^+$ T cell subsets examined over time after 9B12 anti-OX40 monoclonal antibody administration. PBMC collected at different time points from two patients after anti-OX40 infusion and one normal donor after tetanus immunization were analyzed using a multi-color flow cytometry panel described in Example 4. (a) Cells gated on $CD3^+$, $CD95^+$, $CD4^+$ analyzed for FoxP3 and Ki-67. (b) Cells gated on $CD3^+$ $CD95^+$, $CD8^+$ T cells analyzed for CD28 and Ki-67.

Figure 6:
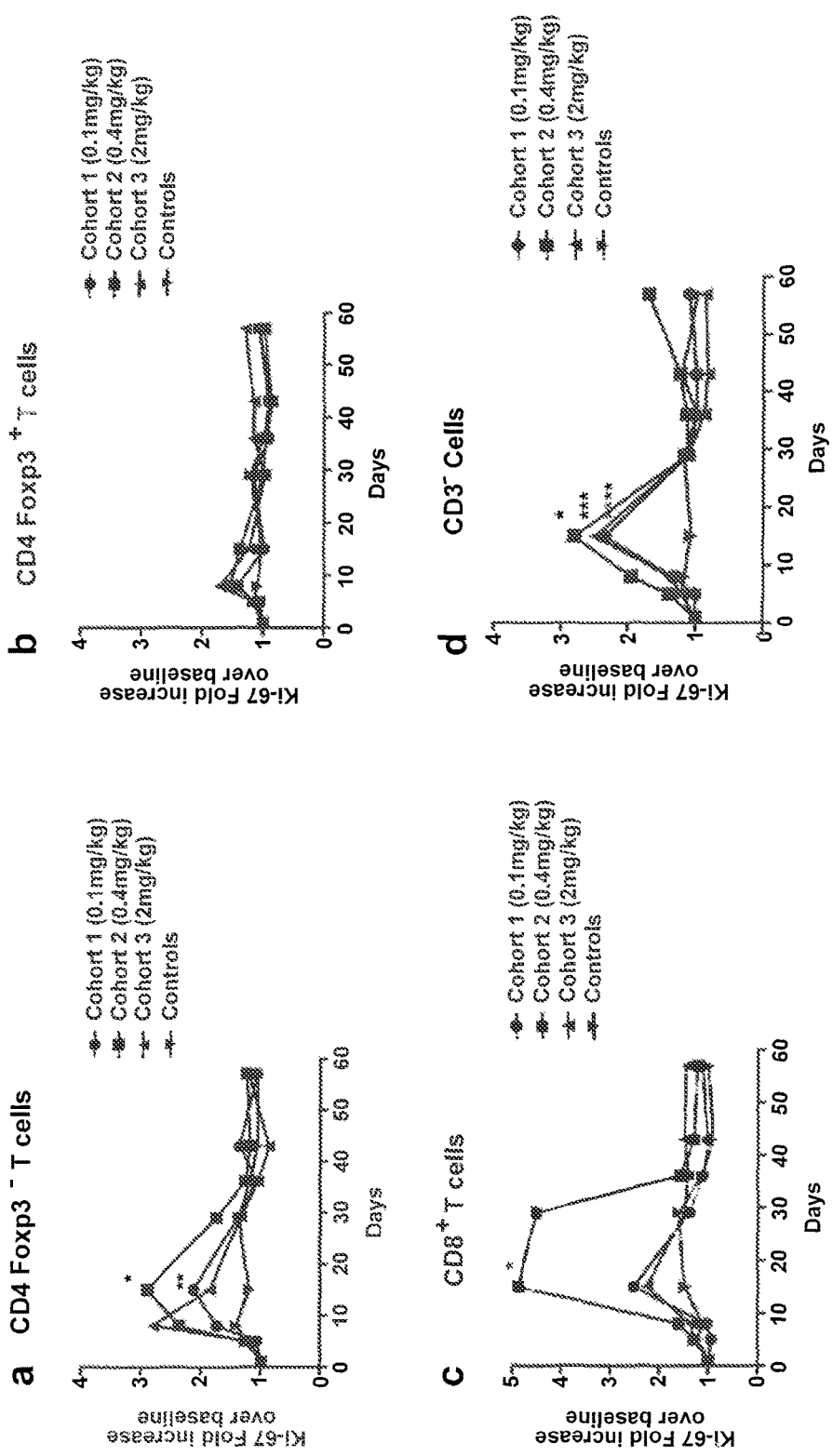

FIG. 6: Average-fold increase in Ki-67 expression for patients in each of the three cohorts and the control group were analyzed. The fold increase was calculated by using the Ki-67 percentages at Day 0 (baseline) and dividing it by the percentage of $Ki-67^+$ cells on various days following anti-OX40 monoclonal antibody administration. (a) Ki-67 fold-increase for $CD4^+$ $Foxp3^{neg}$ T cells, (b) $CD4^+$ $Foxp3^{pos}$ T cells, (c) $CD8^+$ T cells and (d) $CD3^-$ NK cells. Statistical analyses were performed as described in Example 4. * p=0.001,  p=0.013, * p=0.004, **** p=0.007.

Figure 7:
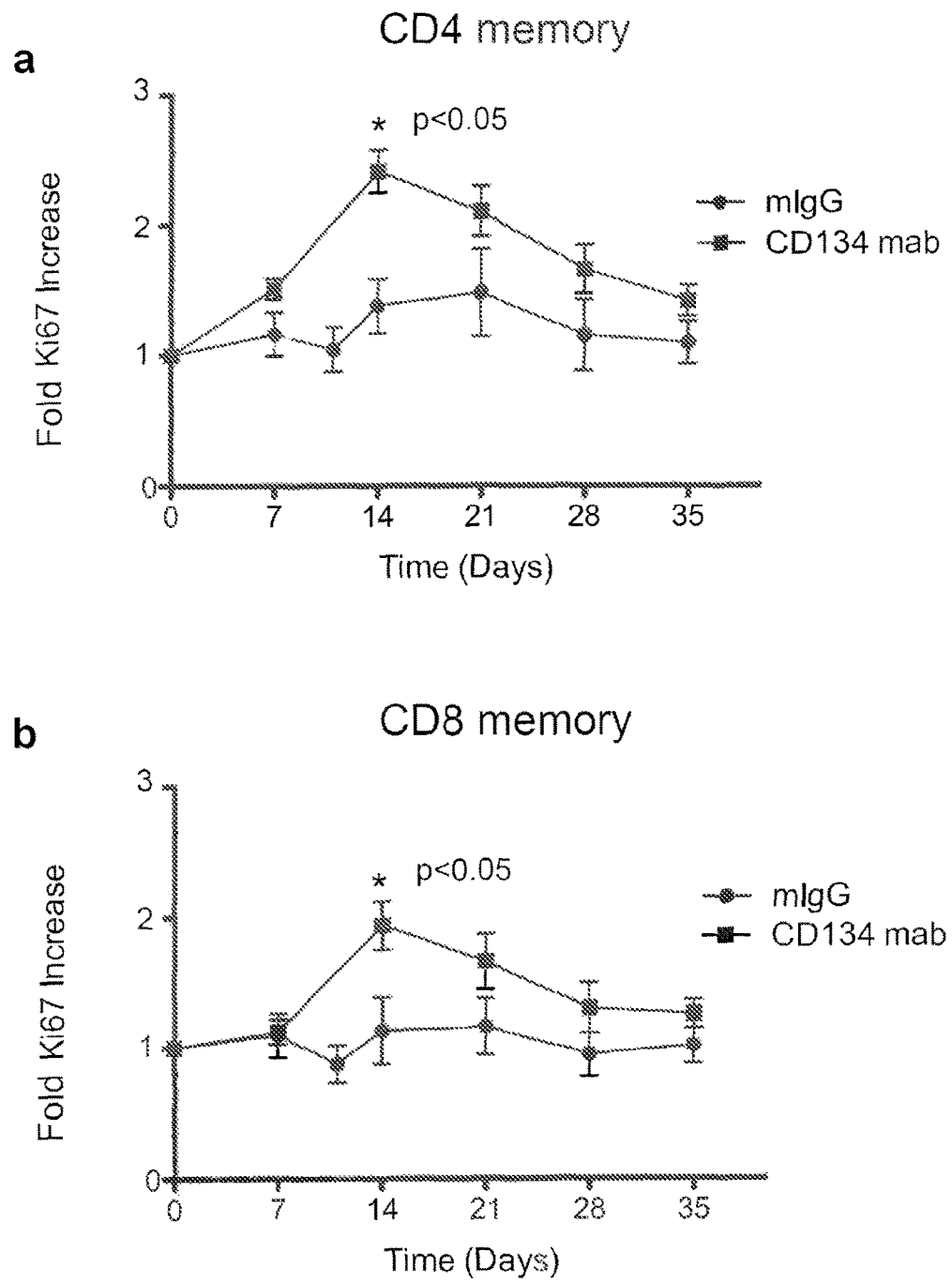

FIG. 7: Ki-67 expression by monkey $CD4^+$ and $CD8^+$ memory T cells after the administration of anti-OX40 or mouse Immunoglobulin. As in FIGS. 5 and 6, the fold-increase of Ki-67 expression was calculated in both $CD4^+$ and $CD8^+$ T cells. Four monkeys per group were immunized with tetanus and received anti-OX40 or mouse Immunoglobulin at 1 mg/kg i.v. (a) Cells gated on $CD3^+$, $CD95^+$ $CD4^+$ T cells, (b) cells gated on $CD3^+$ $CD95^+$ $CD8^+$ and assessed for fold-increase in Ki-67.

Figure 8:
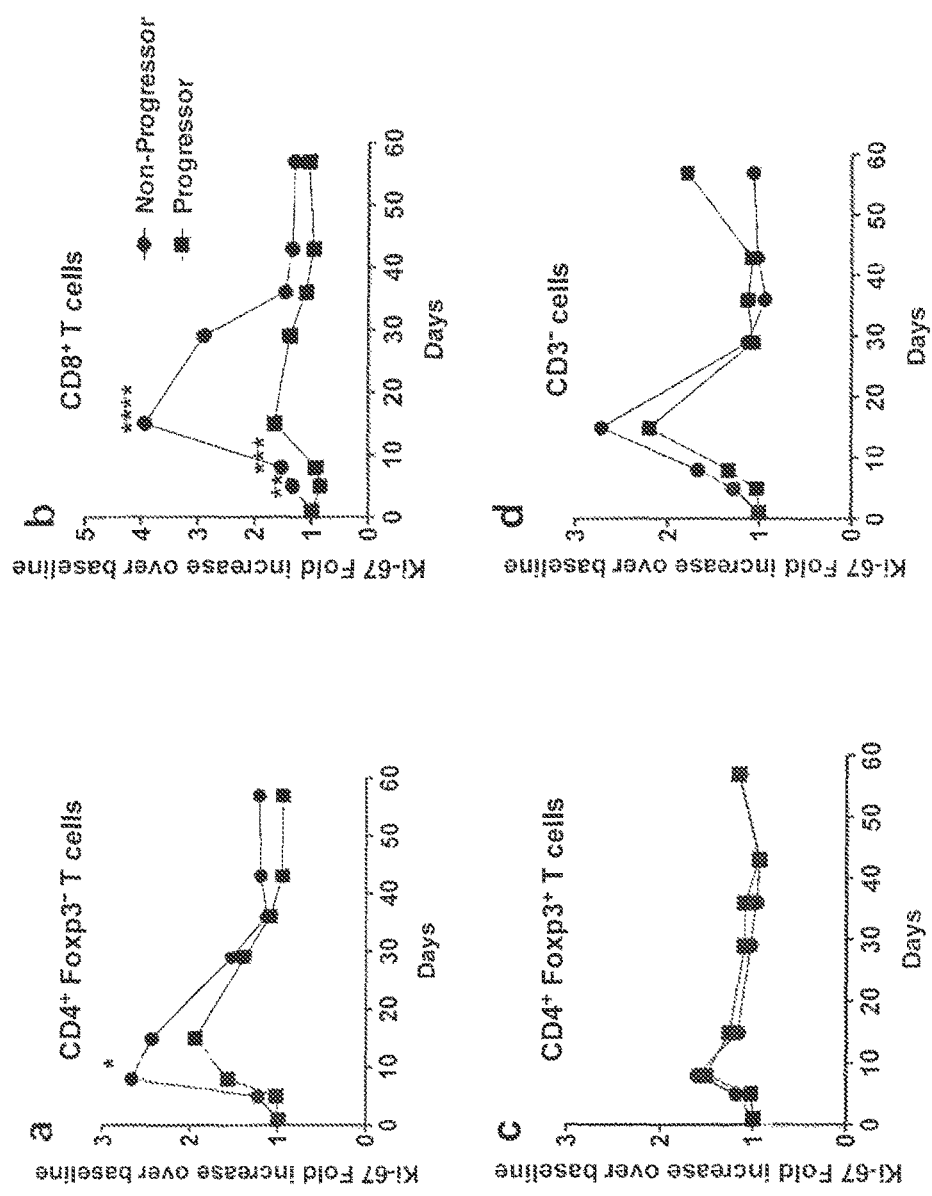

FIG. 8: Patients treated with anti-OX40 monoclonal antibody were stratified into two groups based on progression of disease ("progressors"), n=10 or regression/stabilization of disease ("non-progressors"), n=19. The average-fold increase in Ki-67 expression of PBMC was determined for progressors vs non-progressors in the following four different cell sub-populations; (a) $CD3^+$, $CD95^+$, $CD4^+$ $Foxp3^{neg}$ T cells, (b) $CD3^+$, $CD95^+$, $CD8^+$ T cells, (c) $CD3^+$, $CD95^+$, $CD4^+$ $Foxp3^{pos}$ T cells and (d) $CD3^-$ NK cells. Statistical evaluation was performed to assess significance for each group as detailed in Example 4. *p=0.021,  p=0.003, * p=0.001, **** p=0.01.

Figure 9:
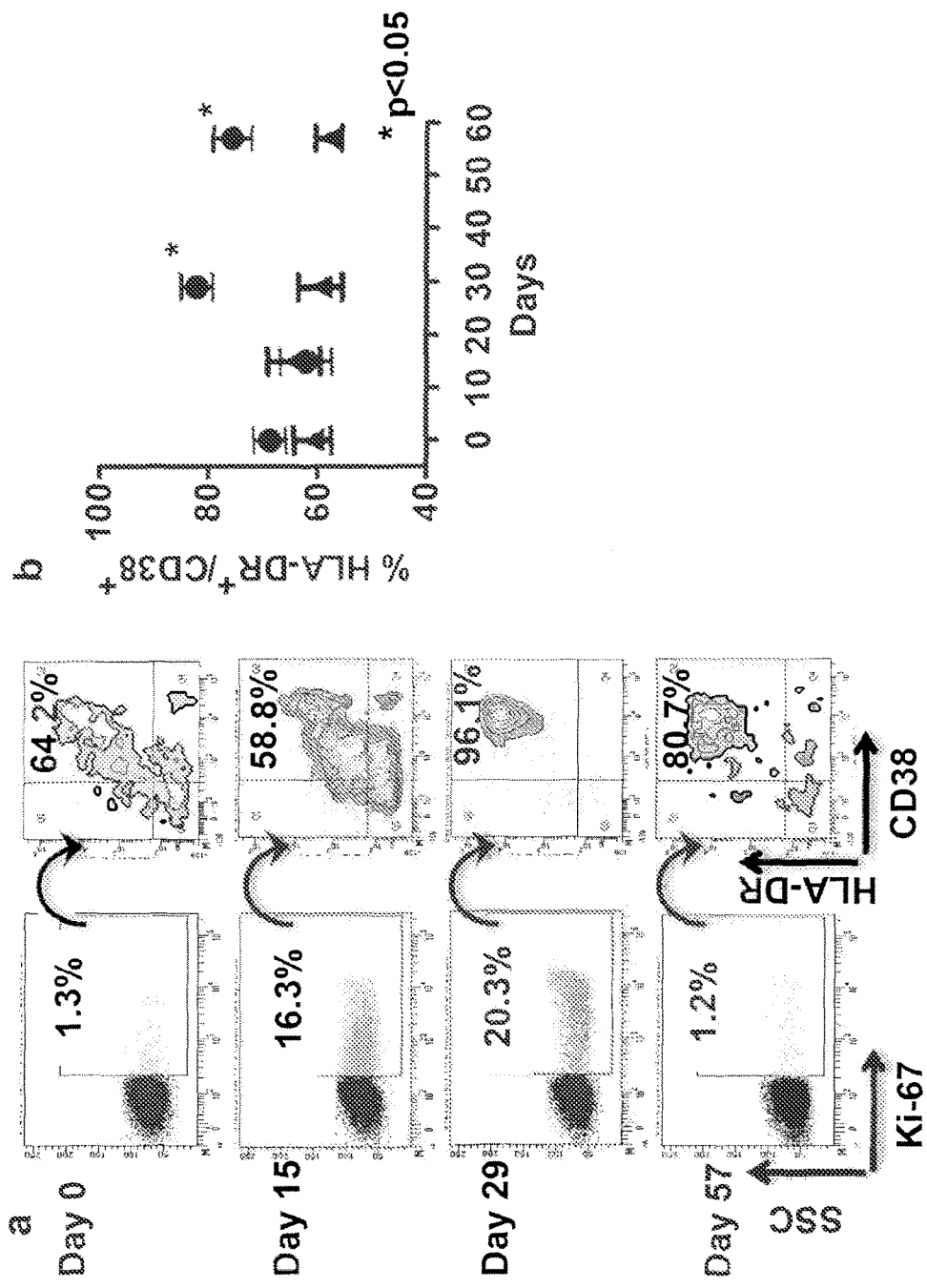

FIG. 9: Anti-OX40 administration increases the expression of HLA-DR and CD38 on cycling $CD8^+$ T cells. (a) PBL gated on $CD3^+$ $CD8^+$ T cells and analyzed for Ki-67 from a patient in the second cohort at different time points after anti-OX40 administration (left column). The right column depicts cells gated on $CD3^+$ $CD8^+$ $Ki-67^+$ (cycling cells) and assessed for expression of the activation markers HLA-DR and CD38 at different times after anti-OX40 administration. (b) Comparison of the mean percent of cycling CD3+ CD8+ that co-express HLA-DR and CD38 T cells in 11 OX40 treated patients randomly selected from all three cohorts (black circles) and 9 normal donors (black triangles).

Figure 10:
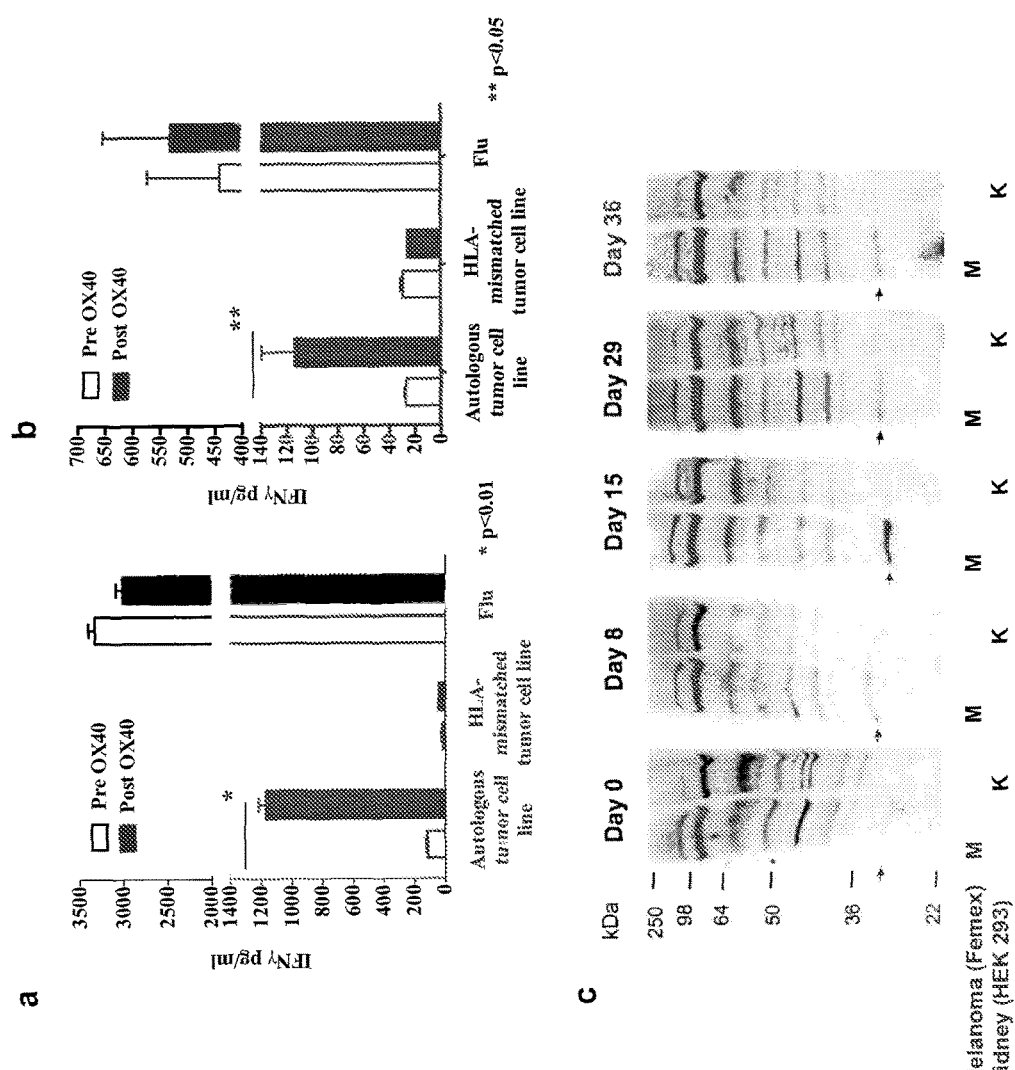

FIG. 10: Anti-OX40 infusion increases tumor-specific immune-response. (a-b) PBMC from two patients with melanoma, prior and post anti-OX40 monoclonal antibody therapy, were co-cultured with either autologous or HLA-mismatched melanoma cell lines and IFN-γ in the supernatant was measured by ELISA. Flu responses, which served as a positive control, were not significantly different in the pre and post samples. Anti-tumor specific antibodies were measured by Western blot (c) serum from a patient with melanoma was used to probe lysates from a melanoma cell line (femex) or a human embryonic kidney cell line (HEK 293) at different time points after anti-OX40 monoclonal antibody administration.

DETAILED DESCRIPTION

1. Definitions

It is to be noted that the term "a" or "an" entity refers to one or more of that entity; for example, "an OX40 agonist" is understood to represent one or more OX40 agonists. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology. Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or embodiments of the disclosure, which can be had by reference to the specification as a whole. Accordingly, the terms defined immediately below are more fully defined by reference to the specification in its entirety.

It is understood that wherever embodiments are described herein with the language "comprising," otherwise analogous embodiments described in terms of "consisting of" and/or "consisting essentially of" are also provided.

The terms "OX40" and "OX40 receptor" are used interchangeably herein. The receptor is also referred to as CD134, ACT-4, and ACT35. OX40 is a member of the TNFR-superfamily of receptors, and is expressed on the surface of antigen-activated mammalian CD4+ and CD8+ T lymphocytes (Paterson, D. J., et al. *Mol Immunol* 24, 1281-1290 (1987); Mallett, S., et al. *EMBO J* 9, 1063-1068 (1990); Calderhead, D. M., et al. *J Immunol* 151, 5261-5271 (1993)).

As used herein, the term OX40 ligand ("OX40L"), also variously termed gp34, ACT-4-L, and CD252, is a protein that specifically interacts with the OX40 receptor (Baum P. R., et al. *EMBO J.* 13:3992-4001(1994)). The term OX40L includes the entire OX40 ligand, soluble OX40 ligand, and fusion proteins comprising a functionally active portion of OX40 ligand covalently linked to a second moiety, e.g., a protein domain. Also included within the definition of OX40L are variants which vary in amino acid sequence from naturally occurring OX4L but which retain the ability to specifically bind to the OX40 receptor. Further included within the definition of OX40L are variants which enhance the biological activity of OX40.

As used herein, an "agonist," e.g., an OX40 agonist is a molecule which enhances the biological activity of its target, e.g., OX40. In a certain aspects blocking OX40 agonists, comprising, e.g., anti-OX40 antibodies or OX40 ligand compositions, substantially enhance the biological activity of OX40. Desirably, the biological activity is enhanced by 10%, 20%, 30%, 50%, 70%, 80%, 90%, 95%, or even 100%. In certain aspects, OX40 agonists as disclosed herein include OX40 binding molecules, e.g., binding polypeptides, e.g., anti-OX40 antibodies, OX40L, or fragments or derivatives of these molecules.

A "binding molecule" or "antigen binding molecule" refers in its broadest sense to a molecule that specifically binds target, e.g., OX40 receptor. In one aspect, a binding molecule is an antibody or an antigen-binding fragment thereof. In another aspect, a binding molecule includes at least one heavy or light chain CDR of a reference antibody molecule. In another aspect, a binding molecule includes at least two, three, four, five, or six CDRs from one or more reference antibody molecules.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

An "OX40 binding molecule" as described herein is an agent which binds substantially only to OX40 present on the surface of mammalian T-cells, such as activated CD4+ T-cells. As used herein, the term "OX40 binding molecule" includes anti-OX40 antibodies and OX40L.

The terms "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "variable region" of an antibody refers to the variable region of the antibody light chain or the variable region of the antibody heavy chain, either alone or in combination. The variable regions of the heavy and light chain each consist of four framework regions (FW) connected by three complementarity determining regions (CDRs) also known as hypervariable regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals.

The term "chimeric antibody" refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc) with the desired specificity, affinity, and functional capability while the constant regions are homologous to the sequences in antibodies derived from another (usually human) to avoid eliciting an immune response in that species.

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the complementary determining region (CDR) are replaced by residues from the CDR of a non-human species (e.g., mouse, rat, rabbit, or hamster) that have the desired specificity, affinity, and capability (Jones et al., 1986, *Nature,* 321:522-525; Riechmann et al., 1988, *Nature,* 332:323-327; Verhoeyen et al., 1988, *Science,* 239:1534-1536). In some instances, the Fv framework region (FW) residues of a human immunoglobulin are replaced with the corresponding residues in an antibody from a non-human species that has the desired specificity, affinity, and capability.

A humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all or substantially all of the CDR regions that correspond to the non-human immunoglobulin whereas all or substantially all of the FW regions are those of a human immunoglobulin consensus sequence. A humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

As used herein, "human" or "fully human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example, in U.S. Pat. No. 5,939,598 by Kucherlapati et al. "Human" or "fully human" antibodies also include antibodies comprising at least the variable domain of a heavy chain, or at least the variable domains of a heavy chain and a light chain, where the variable domain(s) have the amino acid sequence of human immunoglobulin variable domain(s).

"Human" or "fully human" antibodies also include antibodies that comprise, consist essentially of, or consist of, variants (including derivatives). Standard techniques known to those of skill in the art can be used to introduce mutations in the nucleotide sequence encoding a human antibody, including, but not limited to, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3.

The term "anti-OX40 antibodies" and grammatical equivalents encompasses monoclonal and polyclonal antibodies which are specific for OX40, i.e., which bind substantially only to OX40, as well as antigen-binding fragments thereof. In certain aspects, anti-OX40 antibodies as described herein are monoclonal antibodies (or antigen-binding fragments thereof), e.g., murine, humanized, or fully human monoclonal antibodies.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain embodiments, a subject is successfully "treated" for cancer according to the methods described herein if the patient shows, e.g., total, partial, or transient remission of a certain type of cancer.

A subject is successfully "treated" according to the methods of described herein if the patient shows one or more of the following: a reduction in the number of or complete absence of cancer cells; a reduction in the tumor size; or retardation or reversal of tumor growth, inhibition, e.g., suppression, prevention, retardation, shrinkage, or reversal of metastases, e.g., of cancer cell infiltration into peripheral organs including, for example, the spread of cancer into soft tissue and bone; inhibition of, e.g., suppression of, retardation of, prevention of, shrinkage of, reversal of or an absence of tumor metastases; inhibition of, e.g., suppression of, retardation of, prevention of, shrinkage of, reversal of or an absence of tumor growth; relief of one or more symptoms associated with the specific cancer; reduced morbidity and mortality; improvement in quality of life; or some combination of effects. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The terms "cancer", "tumor", "cancerous", and "malignant" refer to or describe the physiological condition in mammals that is typically characterized by unregulated cell growth. Examples of cancers include but are not limited to, melanoma, gastrointestinal cancer, renal cell carcinoma, prostate cancer, and lung cancer.

The terms "metastasis," "metastases," "metastatic," and other grammatical equivalents as used herein refer to cancer cells which spread or transfer from the site of origin (e.g., a primary tumor) to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures. The terms also refer to the process of metastasis, which includes, but is not limited to detachment of cancer cells from a primary tumor, intravasation of the tumor cells to circulation, their survival and migration to a distant site, attachment and extravasation into a new site from the circulation, and microcolonization at the distant site, and tumor growth and development at the distant site. In certain aspects, metastases appear in sites including, but not limited to lymph node, lung, liver, and bone.

By "subject" or "individual" or "animal" or "patient" or "mammal," is meant any subject, particularly a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purpose of this disclosure, as are native or recombinant polypeptides that have been separated, fractionated, or partially or substantially purified by any suitable technique.

Also included as polypeptides are fragments, derivatives, analogs, or variants of the foregoing polypeptides, and any combination thereof. The terms "fragment," "variant," "derivative," and "analog" when referring, e.g., to OX40 agonist polypeptides include any polypeptides that retain at least some of the binding properties of the corresponding OX40 agonist. Fragments of polypeptides include proteolytic fragments, as well as deletion fragments, in addition to specific antibody fragments discussed elsewhere herein. As used herein a "derivative," e.g., of an OX40 agonist polypeptide refers to a subject polypeptide having one or more residues chemically derivatized by reaction of a functional side group. Also included as "derivatives" are those peptides that contain one or more naturally occurring amino acid derivatives of the twenty standard amino acids.

The terms "T cell" and "T-lymphocyte" are used interchangeably herein to refer to the population of lymphocytes carrying a T cell receptor complex (including the T-cell-specific CD3 marker) on the cell surface. While T-lymphocytes very generally function in cell-mediated immunity, they can be divided into myriad sub-populations based not only on their particular functions, but also on the differential expression of certain surface and intracellular antigens, which can function as "markers" for particular T-lymphocyte sub-populations. As a general non-limiting example, helper T-cells express the surface antigen CD4, where cytotoxic T-cells express CD8. Sub-populations within these groups, and overlapping between these groups can be identified by other cell surface markers including, but not limited to CD95, CD25, FoxP3, CD28, CCR7, CD127, CD38, HLA-DR, and Ki-67. Subpopulations of T-lymphocytes can be identified and/or isolated from a mixed population of blood cells through the use of labeled antibodies, e.g., through flow cytometry or fluorescence activated cell sorting, described in more detail in the examples below. For example helper T cells can be identified as expressing CD3 and CD4, but not FoxP3. Other overlapping and non-overlapping subpopulations of T-lymphocytes include memory T cells, immature T cells, mature T cells, regulatory T cells (Tregs), activated T cells, and natural killer T (NKT) cells.

"Ki-67" (also known as MK167) is a nuclear antigen marker expressed in proliferating cells but not in resting cells. While not specific for T-lymphocytes, detection of Ki-67 in combination with T-lymphocyte-specific markers can be used to assay the level of proliferation within a subject's T-cells, or a subpopulation thereof.

As used herein, an increase in Ki-67 expression within a subject's T-lymphocytes or a subpopulation thereof can be measured in comparison to a "corresponding baseline level." A certain small fraction of an individual's T-lymphocytes will normally be undergoing proliferation For example, in normal human blood about 1.5% of $CD3^+$ lymphocytes (i.e., mature T cells) are Ki-$67^+$ (Cordone, I., et al. *J. Clin. Pathol* 45:201-205 (1992)). Thus, in one embodiment the "corresponding baseline level" for Ki-$67^+$ T lymphocytes is about 1.5% of total T-lymphocytes. Similarly, a person of ordinary skill in the art can easily determine the corresponding baseline level for any subpopulation of T-lymphocytes from peripheral blood lymphocytes (PBLs) of normal human subjects. For example, according to this embodiment PBLs from a panel of health human volunteers can be screened determine the average number of T helper cells, i.e., $CD3^+$ $CD4^+$ FoxP3 cells, which are positive for Ki-67, to determine the "corresponding baseline level" for the population of $CD3^+$ CD4+ FoxP3$^-$ T-lymphocytes.

In certain embodiments, the "corresponding baseline level" of Ki-67 expression is measured in a population of patients suffering from a disease. For example, in order to measure an increase in Ki-67 expression in a cancer patient in response to a treatment, e.g., administration of an OX40 agonist, the "corresponding baseline level" of Ki-67 expression in T-lymphocytes or a subpopulation thereof can be determined by measuring the average Ki-67 expression level in the T-lymphocytes or a subpopulation thereof from a population of patients suffering from the same or similar cancer, who have not received an OX40 agonist.

In yet another embodiment, in order to measure an increase in Ki-67 expression in a cancer patient in response to a treatment, e.g., administration of an OX40 agonist, the "corresponding baseline level" of Ki-67 expression in T-lymphocytes or a subpopulation thereof can be determined by obtaining PBLs from the patient prior to treatment, and determining the actual Ki-67 expression level in the patient's T-lymphocytes, or subpopulation thereof, thereby establishing the patient's actual "corresponding baseline level."

II. OX40 Agonists

OX40 agonists interact with the OX40 receptor on $CD4^+$ T-cells during, or shortly after, priming by an antigen results in an increased response of the $CD4^+$ T-cells to the antigen. In the context of the present disclosure, the term "agonist" refers to molecules which bind to and stimulate at least one activity mediated by the OX40 receptor. For example, an OX40 agonist interacting with the OX40 receptor on antigen specific $CD4^+$ T-cells can increase T cell proliferation as compared to the response to antigen alone. The elevated response to the antigen can be maintained for a period of time substantially longer than in the absence of an OX40 agonist. Thus, stimulation via an OX40 agonist enhances the antigen specific immune response by boosting T-cell recognition of antigens, e.g., tumor cells. OX40 agonists are described, for example, in U.S. Pat. Nos. 6,312,700, 7,504, 101, 7,622,444, and 7,959,925, which are incorporated herein by reference in their entireties.

OX40 agonists include, but are not limited to OX40 binding molecules, e.g., binding polypeptides, e.g., OX40 ligand ("OX40L") or an OX40-binding fragment, variant, or derivative thereof, such as soluble extracellular ligand domains and OX40L fusion proteins, and anti-OX40 antibodies (for example, monoclonal antibodies such as humanized monoclonal antibodies), or an antigen-binding fragment, variant or derivative thereof. Examples of anti-OX40 monoclonal antibodies and are described in WO 95/12673 and WO/95/21915, the disclosures of which are incorporated herein by reference in their entireties. In certain aspects, the anti-OX40 monoclonal antibody is 9B12, or an antigen-binding fragment, variant, or derivative thereof, as described in Weinberg, A. D., et al. *J Immunother* 29, 575-585 (2006), which is incorporated herein by reference in its entirety.

In one aspect, an OX40 agonist includes a fusion protein in which one or more domains of OX40L is covalently linked to one or more additional protein domains. Exemplary OX40L fusion proteins that can be used as OX40 agonists are described in U.S. Pat. No. 6,312,700, the disclosure of which is incorporated herein by reference in its entirety.

In one aspect, an OX40 agonist includes an OX40L fusion polypeptide that self-assembles into a multimeric (e.g., trimeric or hexameric) OX40L fusion protein. Such fusion proteins are described, e.g., in U.S. Pat. No. 7,959,925, which is incorporated by reference herein in its entirety. The multimeric OX40L fusion protein exhibits increased efficacy in enhancing antigen specific immune response in a subject, particularly a human subject, due to its ability to spontaneously assemble into highly stable trimers and hexamers.

In certain aspects, an OX40 agonist capable of assembling into a multimeric form includes a fusion polypeptide comprising in an N-terminal to C-terminal direction: an immunoglobulin domain, wherein the immunoglobulin domain includes an Fc domain, a trimerization domain, wherein the trimerization domain includes a coiled coil trimerization domain, and a receptor binding domain, wherein the receptor binding domain is an OX40 receptor binding domain, e.g., an OX40L or an OX40-binding fragment, variant, or derivative thereof, where the fusion polypeptide can self-assemble into a trimeric fusion protein. In one aspect, an OX40 agonist capable of assembling into a multimeric form is capable of binding to the OX40 receptor and stimulating at least one OX40 mediated activity. In certain aspects, the OX40 agonist includes an extracellular domain of OX40 ligand.

The trimerization domain of an OX40 agonist capable of assembling into a multimeric form serves to promote self-assembly of individual OX40L fusion polypeptide molecules into a trimeric protein. Thus, an OX40L fusion polypeptide with a trimerization domain self-assembles into a trimeric OX40L fusion protein. In one aspect, the trimerization domain is an isoleucine zipper domain or other coiled coli polypeptide structure. Exemplary coiled coil trimerization domains include: TRAF2 (GENBANK® Accession No. Q12933, amino acids 299-348; Thrombospondin 1 (Accession No. PO7996, amino acids 291-314; Matrilin-4 (Accession No. 095460, amino acids 594-618; CMP (matrilin-1) (Accession No. NP—002370, amino acids 463-496; HSF1 (Accession No. AAX42211, amino acids 165-191; and Cubilin (Accession No. NP—001072, amino acids 104-138. In certain specific aspects, the trimerization domain includes a TRAF2 trimerization domain, a Matrilin-4 trimerization domain, or a combination thereof.

It can further be desirable to modify an OX40 agonist in order to increase its serum half-life. For example, the serum half-life of an OX40 agonist can be increased by conjugation to a heterologous molecule such as serum albumin, an antibody Fc region, or PEG. In certain embodiments, OX40 agonists can be conjugated to other therapeutic agents or toxins to form immunoconjugates and/or fusion proteins. In certain aspects, an OX40 agonist can be conjugated to an agent selected from the group that includes a therapeutic agent, a prodrug, a peptide, a protein, an enzyme, a virus, a lipid, a biological response modifier, or a pharmaceutical agent. Suitable toxins and chemotherapeutic agents are described in Remington's Pharmaceutical Sciences, 19th Ed. (Mack Publishing Co. 1995), and in Goodman and Gilman's the Pharmacological Basis of Therapeutics, 7th Ed. (MacMillan Publishing Co. 1985). Other suitable toxins and/or chemotherapeutic agents are known to those of skill in the art.

In certain aspects, an OX40 agonist can be formulated so as to facilitate administration and promote stability of the active agent. In certain aspects, pharmaceutical compositions in accordance with the present disclosure comprise a pharmaceutically acceptable, non-toxic, sterile carrier such as physiological saline, non-toxic buffers, preservatives and the like. Suitable formulations for use in the treatment methods disclosed herein are described, e.g., in Remington's Pharmaceutical Sciences (Mack Publishing Co.) 16th ed. (1980).

III. Methods for Treating Cancer

Provided herein are methods for treating cancer, comprising administration of an OX40 agonist, either alone or in combination with other cancer treatments. Administration of an OX40 agonist results in an enhanced T-lymphocyte response to antigens on a variety of cancer cells, because the activation of OX40, while functioning in concert with antigenic stimulation of T-lymphocytes, is not antigen or cell-specific itself.

One aspect of the disclosure provides a method for treating cancer, comprising administering to a patient in need of treatment an effective amount of an OX40 agonist. The administration can stimulate the proliferation of certain sub-populations of T-lymphocytes. The Ki-67 marker is strictly associated with proliferating cells. Accordingly, T cell proliferation can be measured as an increase in expression of the Ki-67 marker in the patient's T-cells, or a sub-population thereof. According to this method, an effective administration of an OX40 agonist increases the level of Ki-67 expression in T-lymphocytes of the patient, or a subpopulation thereof over a corresponding baseline level, and can stimulate T-lymphocyte activity against cancer cells in the patient.

Another aspect of the disclosure provides a method for treating cancer, comprising administering to a patient in need of treatment an effective amount of an OX40 agonist as noted above; and detecting the level of Ki-67 expression in the patient's T-lymphocytes, or a subpopulation thereof, where the T-lymphocytes are obtained at one or more time points following the administration, e.g., through a blood draw, enrichment for PBMCs, and detecting Ki-67 expression levels in the patient's T-lymphocytes or subpopulation thereof via flow cytometry. An increase in the Ki-67 expression level is determined relative to corresponding baseline level as described elsewhere herein. According to this aspect, the administration of an OX40 agonist can stimulate T-lymphocyte activity against the cancer cells in the patient. Furthermore, an increase in the Ki-67 expression level in the patient's T-lymphocytes or subpopulation thereof compared to a corresponding baseline level can be prognostic of effective treatment.

As noted in the Examples below, human patients suffering from advanced stages of a variety of different solid tumor cancers were administered an OX40 agonist, namely an anti-OX40 monoclonal antibody, and certain of the patients showed favorable outcomes in response to the treatment, e.g., varying levels of tumor regression, shrinkage, or a stalling in the advancement of the disease. It was found that an increase in Ki-67 expression in the patients' overall T-lymphocytes, or in certain $CD4^+$ and $CD8^+$ subpopulations of T-lymphocytes, correlated with a favorable outcome, e.g., tumor shrinkage or regression, or a reduction in disease progression. According to this aspect, a healthcare provider can then monitor Ki-67 expression in a patient's T-lymphocytes or a subpopulation thereof and in the absence of a significant increase in Ki-67 expression, adjust the OX40 agonist dose or alter the prescribed therapy in other ways or stop treatment with an OX40 agonist.

In certain specific aspects, a method of treating cancer is provided in which an effective amount of an OX40 agonist is administered to a patient in need of treatment by a primary care provider, e.g., a physician or other healthcare provider or a hospital, and the primary care provider then obtains T-lymphocytes from the patient at one or more time points following administration, e.g., by drawing blood, which can then be processed either by the healthcare provider or a clinical laboratory to isolate peripheral blood mononuclear leukocytes (PBMCs). In certain aspects, an OX40 agonist is self-administered by the patient as part of a home care kit. Such a home care kit can, in some instances, further allow the patient to self-obtain a blood sample. The healthcare provider or patient can them submit the samples to a laboratory, e.g., an independent clinical laboratory, for detection of the level of Ki-67 expression in the T-lymphocytes or a subpopulation thereof and comparison to a corresponding baseline level of Ki-67 expression, by methods described elsewhere herein, and the results would be transmitted to the healthcare provider. As described above, the administration of an OX40 agonist can stimulate T-lymphocyte activity against the cancer cells in the patient. Furthermore, an increase in the Ki-67 expression level in the patient's T-lymphocytes or subpopulation thereof compared to a corresponding baseline level, as described above, can be prognostic of effective treatment.

In certain aspects, the administration of an OX40 agonist, the obtaining of T-lymphocytes at one or more time periods following administration, the detection of the level of Ki-67 expression in the T-lymphocytes or a subpopulation thereof, the comparison to corresponding baseline level of Ki-67 expression, and the determination of whether an increase in Ki-67 expression over a corresponding baseline has occurred, can all be carried out by a single entity, e.g., a hospital or physician's office with an internal clinical laboratory.

Any increase in Ki-67 expression in the T-lymphocytes or a subpopulation thereof can be prognostic of effective treatment. In certain aspects, a favorable prognosis can correlate with an increase the level of Ki-67 expression in T-lymphocytes or a subpopulation thereof by at least about 0.5-fold, at least about 1-fold, at least about two-fold, at least about four-fold, at least about 6-fold, at least about 8-fold, or even at least about 10-fold or more over the corresponding baseline level.

In certain embodiments of the methods described above, the Ki-67 expression levels in the patient's $CD4^+$ $FoxP3^+$ subpopulation of T lymphocytes (Treg cells) does not increase.

T-lymphocytes or a subpopulation thereof can be obtained from the cancer patient at various time points following administration of the OX40 agonist, samples can be obtained several times a day for one or more days, once a day for one or more days, every two days, every three days, every four days, every five days, every six days, every week, every two weeks, and so on, for a time period following administration ranging from one day out to several months or even a year.

An effective amount of an OX40 agonist to be administered can be determined by a person of ordinary skill in the art by well-known methods. For example, in certain aspects an effective dose of an OX40 agonist, e.g., an anti-OX40 monoclonal antibody, is about 0.01 mg/kg to about 10 mg/kg, e.g., about 0.1 mg/kg, 0.4 mg/kg or 2 mg/kg of anti-OX40 mAb. The OX40 agonist can be administered as a single dose or as multiple doses, e.g., at least two, three, four, five, six or more doses, spaced at various time intervals to be determined by the attending physician, e.g., one or more doses a day, one or more doses every three days, one or more doses every five days, one or more doses every week, and so on. Treatment can continue or can be varied based on monitoring of efficacy (see below) for length of time to provide the most benefit to the patient being treated.

Clinical response to administration of an OX40 agonist can also be assessed using screening techniques such as magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with an OX40 agonist may experience the beneficial effect of an improvement in the symptoms associated with the disease.

Administration of the OX40 agonist can be via any usable route, as determined by the nature of the formulation and the needs of the patient. In certain embodiments, the OX40 agonist is administered by IV infusion.

Given that immune stimulation with OX40 agonists is not antigen-specific, a variety of cancers can be treated by the methods provided herein, for example in certain aspects, the cancer is a solid tumor, or a metastasis thereof. Types of cancers include, but are not limited to melanoma, gastrointestinal cancer, renal cell carcinoma, prostate cancer, lung cancer, or any combination thereof. The site of metastasis is not limiting and can include, for example metastases in the lymph node, lung, liver, bone, or any combination thereof.

The cancer treatment methods provided herein can also include other conventional or non-conventional cancer treatments in addition to the administration of an OX40 agonist. By non-limiting example, administration of an OX40 agonist can be combined with surgery, radiation, chemotherapy, immunotherapy, targeting anti-cancer therapy, hormone therapy, or any combination thereof. The additional cancer therapy can be administered prior to, during, or subsequent to the administration of an OX40 agonist. Thus, where the combined therapies comprise administration of an OX40 agonist in combination with administration of another therapeutic agent, as with chemotherapy, radiation therapy, other anti-cancer antibody therapy, small molecule-based cancer therapy, or vaccine/immunotherapy-based cancer therapy, the methods described herein encompass coadministration, using separate formulations or a single pharmaceutical formulation, with simultaneous or consecutive administration in either order.

In certain methods of treating cancer as provided herein, the patient is a human patient. Effective treatment with an OX40 agonist as described herein can include any favorable occurrence, e.g., reducing the rate of progression of the cancer, retardation or no increase in tumor or metastatic growth, stabilization of disease, tumor shrinkage, or tumor regression, either at the site of a primary tumor, or in one or more metastases.

In certain aspects of the cancer treatment methods provided herein the subpopulation of T-lymphocytes is effector T-lymphocytes. In certain aspects of the cancer treatment methods provided herein the subpopulation of T-lymphocytes is memory T-lymphocytes. In certain aspects of the cancer treatment methods provided herein the subpopulation of T-lymphocytes includes those T-lymphocytes which respond to a tumor-specific antigen. As would be readily understood by a person of ordinary skill in the art, the level of Ki-67 expression over baseline in various different subpopulations of T-lymphocytes can be measured by determination of expression of Ki-67 in combination with other T-lymphocyte marker antigens including, but not limited to, CD3, CD4, CD8, FoxP3, CD28, CD95, CD38, and HLA-DR.

In other aspects, the subpopulation of T-lymphocytes is $CD4^+$ $Foxp3^-$ T-lymphocytes. According to this aspect, the increase in the level of Ki-67 expression in the $CD4^+$ $Foxp3^-$ T-lymphocytes is first detected at a time point of less than about one week from the OX40 agonist administration, e.g., 1, 2, 3, 4, 5 or six days after the OX40 agonist administration.

In other aspects the subpopulation of T-lymphocytes is $CD8^+$ T-lymphocytes. According to this aspect the increase in the level of Ki-67 expression in the $CD8^+$ T-lymphocytes is first detected at a time point of at least about one week from the OX40 agonist administration, e.g., 7, 8, 9, 10, 11, 12, 13, days or two weeks or more after the OX40 agonist administration.

In certain aspects where the subpopulation of T-lymphocytes is $CD8^+$ T-lymphocytes, the administration of an OX40 agonist further increases the levels of CD38 expression, HLA-DR expression, or both CD38 and HLA-DR expression. In certain aspects where the subpopulation of T-lymphocytes is $CD8^+$ T-lymphocytes, the administration of an OX40 agonist can increase Ki-67 expression in both CD28 positive and CD28 negative populations in the time period up to about 15 days, e.g., about 10 days, 11 days, 12 days, 13 days, 14 days, 15 days, 16 days, 17 days, or 18 days, but later following administration of the OX40 agonist, e.g. by about 28 days, e.g., about 25 days, 26 days, 27 days, 28 days, 29 days, 30 days, or more; Ki-67 expression levels can be increased primarily in the $CD28^+$ subpopulation of $CD8^+$ T-lymphocytes.

In certain aspects, administration of an OX40 agonist can also increase Ki-67 expression in non-T-lymphocytes, e.g., $CD3^-$ cells such as NK cells, according to this aspect, for example, Ki-67 expression is increased over baseline in $CD3^-$ $CD56^+$ cells.

IV. Methods of Monitoring a Patient's Response to Treatment

This disclosure further provides a method of monitoring whether a cancer patient who has been administered an OX40 agonist will respond to treatment with the OX40 agonist. A variety of OX40 agonists are described elsewhere herein, including, but not limited to OX40 ligands or OX40-binding fragments, variants, or derivatives thereof, and anti-OX40 antibodies or OX40-binding fragments, variants, or derivatives thereof.

In once aspect, the method includes: (a) detecting the level of Ki-67 expression in the patient's T-lymphocytes, or a subpopulation thereof, from samples obtained from the patient at one or more time points following administration of the OX40 agonist; and (b) comparing the level of Ki-67 expression to a corresponding baseline level of Ki-67 expression, wherein an increase over baseline in the level of Ki-67 expression in the T-lymphocytes or subpopulation thereof obtained following administration of the OX40 agonist identifies a patient who will respond to treatment with an OX40 agonist, or indicates that the patient will respond to treatment with an OX40 agonist. Methods of detecting Ki-67 expression in a patient's T-lymphocytes are described elsewhere herein, as are methods of establishing baseline levels of Ki-67 expression. Likewise, treatment methods involving administration of an OX40 agonist are described elsewhere herein.

In a similar aspect, the disclosure provides a method of monitoring whether a cancer patient will respond to treatment with the OX40 agonist, comprising: (a) administering to a cancer patient an effective amount of an OX40 agonist; (b) detecting the level of Ki-67 expression in the patient's T-lymphocytes, or a subpopulation thereof, obtained from the patient at one or more time points following administration of the OX40 agonist; and (c) comparing the level of Ki-67 expression to a corresponding baseline level of Ki-67 expression, wherein an increase over baseline in the level of Ki-67 expression in the T-lymphocytes or subpopulation thereof obtained following administration of the OX40 agonist identifies a patient who will respond to treatment with an OX40 agonist. Methods of administering an OX40 agonist as described elsewhere herein include, e.g., IV infusion of one or more doses or the OX40 agonist.

In certain aspects the monitoring methods provided herein are conducted by a laboratory, e.g., an independent clinical laboratory or other establishment which conducts monitoring assays. According to this aspect, the laboratory can instruct a healthcare professional, e.g., an attending physician or other hospital personnel, or a physician's office, or the patient using a home care kit, to administer an effective amount of an OX40 agonist to a cancer patient in need thereof, and they carry out the detecting and comparison steps as outlined above to determine whether the patient being treated will respond to the treatment, i.e., where the patient's T-lymphocytes or a subpopulation thereof exhibit an increase in Ki-67 expression over baseline.

In certain other aspects the monitoring methods provided herein are conducted by a healthcare provider, e.g., a hospital or physician's office. According to this aspect, the healthcare provider can administer an effective amount of an OX40 agonist to a patient in need of treatment, and obtain T-lymphocyte samples from the patient at one or more time intervals following treatment, e.g., by drawing blood samples and processing the samples to enrich for PBMCs. The healthcare provider can then submit the T-lymphocytes to a facility set up to measure Ki-67 expression levels, e.g., an in-office laboratory, a laboratory that is part of the same hospital, or an independent clinical laboratory, for detection of the level of Ki-67 expression in the T-lymphocytes or a subpopulation thereof and comparison to a corresponding baseline level of Ki-67 expression, which can carry out the detecting and comparison steps as outlined above to determine whether the patient being treated will respond to the treatment, i.e., where the patient's T-lymphocytes or a subpopulation thereof exhibit an increase in Ki-67 expression over baseline.

According to the monitoring methods described herein, an outcome in which the Ki-67 expression levels in the patient's T-lymphocytes or subpopulation thereof increase indicates that the patient is likely responding to treatment. If no increase in Ki-67 expression is observed, a conclusion can be made that the patient is likely not responding to treatment, and the treatment can be adjusted or discontinued as may be determined by the attending healthcare professional. The amount of increase over baseline can be used as measure of the level of response, and in certain aspects, the dosage, frequency of dosage, or route of dosage to the patient can be adjusted to increase the efficacy of the treatment. Timing of dosages, amounts of dosages, and methods of administration are described elsewhere herein.

According to the monitoring methods described herein, any increase in Ki-67 expression in the T-lymphocytes or a subpopulation thereof of the patient can indicate that the patient is responding to treatment. In certain aspects, a favorable response to treatment can correlate with an increase the level of Ki-67 expression in T-lymphocytes or a subpopulation thereof by at least about 0.5-fold, at least about 1-fold, at least about two-fold, at least about four-fold, at least about 6-fold, at least about 8-fold, or even at least about 10-fold or more over the corresponding baseline level.

In certain embodiments of the monitoring methods described above, the Ki-67 expression levels in the patient's $CD4^+$ $FoxP3^+$ subpopulation of T lymphocytes (Treg cells) are not indicative of a response to treatment.

According to the monitoring methods provided herein, T-lymphocytes or a subpopulation thereof can be obtained from the cancer patient at various time points following administration of the OX40 agonist, samples can be obtained several times a day for one or more days, once a day for one or more days, every two days, every three days, every four days, every five days, every six days, every week, every two weeks, and so on, for a time period following administration ranging from one day out to several months or even a year.

An effective amount of an OX40 agonist to be administered can be determined by a person of ordinary skill in the art by well-known methods. Examples of effective doses are provided elsewhere herein, e.g., in the Examples below. According to the monitoring methods provided herein, the continuing dosage to be administered to a patient can be adjusted based on the extent of increase in Ki-67 expression observed in the patient's T-lymphocytes following one or more prior administrations of an OX40 agonist. Based on the monitoring results, additional doses of the OX40 agonist can be administered as a e.g., at least two, three, four, five, six or more doses, spaced at various time intervals to be determined by the attending physician based entirely or in part on the results of the monitoring methods provided herein. Based on the monitoring, treatment can continue or can be varied to provide the most benefit to the patient being treated.

Administration of the OX40 agonist can be via any usable route, as determined by the nature of the formulation and the needs of the patient. In certain embodiments, the OX40 agonist is administered by IV infusion.

The methods provided herein can be used to monitor the efficacy of OX40 agonist treatment of a variety of cancers, for example in certain aspects, the cancer can be a solid tumor, or a metastasis thereof. Types of cancers include, but are not limited to melanoma, gastrointestinal cancer, renal cell carcinoma, prostate cancer, lung cancer, or any combination thereof. The site of metastasis is not limiting and can include, for example metastases in the lymph node, lung, liver, bone, or any combination thereof.

In certain aspects of the monitoring methods provided herein, the level of Ki-67 expression over baseline is measured in the subpopulation of effector T-lymphocytes. In certain aspects of the monitoring methods provided herein, the level of Ki-67 expression over baseline is measured in the subpopulation of memory T-lymphocytes. In certain aspects of the monitoring methods provided herein, the level of Ki-67 expression over baseline is measured in the subpopulation of T-lymphocytes which respond to a tumor-specific antigen. As would be readily understood by a person of ordinary skill in the art, the level of Ki-67 expression over baseline in various different subpopulations of T-lymphocytes can be measured by determination of expression of Ki-67 in combination with other T-lymphocyte marker antigens including, but not limited to, CD3, CD4, CD8, FoxP3, CD28, CD95, CD38, and HLA-DR. Such determinations can be accomplished through the use of specific antibodies to T-cell markers, e.g., labeled antibodies such as fluorescently labeled antibodies, in an assay such as flow cytometry.

In other aspects, the subpopulation of T-lymphocytes to be monitored can be CD4$^+$ Foxp3$^-$ T-lymphocytes or CD4$^+$ CD95$^+$ Foxp3$^-$ T-lymphocytes. According to this aspect, the increase in the level of Ki-67 expression in the CD4$^+$ Foxp3' T-lymphocytes is first detected at a time point of less than about one week from the OX40 agonist administration, e.g., 1, 2, 3, 4, 5 or six days after the OX40 agonist administration.

In other aspects the subpopulation of T-lymphocytes is CD8$^+$ T-lymphocytes. According to this aspect the increase in the level of Ki-67 expression in the CD8$^+$ T-lymphocytes is typically first detected at a time point of at least about one week from the OX40 agonist administration, e.g., 7, 8, 9, 10, 11, 12, 13, days or two weeks or more after the OX40 agonist administration.

In certain aspects where the subpopulation of T-lymphocytes is CD8$^+$ T-lymphocytes, the administration of an OX40 agonist further increases the levels of CD38 expression, HLA-DR expression, or both CD38 and HLA-DR expression. In certain aspects where the subpopulation of T-lymphocytes is CD8$^+$ T-lymphocytes, an increase in Ki-67 expression can be monitored or detected in both CD28$^+$ and CD28$^-$ CD8$^+$ T-lymphocytes at about 15 days, e.g., about 10 days, 11 days, 12 days, 13 days, 14 days, 15 days, 16 days, 17 days, or 18 days. In certain aspects where the subpopulation of T-lymphocytes is CD8$^+$ T-lymphocytes, an increase in Ki-67 expression can be monitored or detected primarily in CD28$^+$ CD8$^+$ T-lymphocytes for a longer period of time, e.g., up to about 28 days, e.g., about 25 days, 26 days, 27 days, 28 days, 29 days, 30 days, or more.

In certain aspects, an increase in Ki-67 expression levels can also be monitored in non-T-lymphocytes, e.g., CD3$^-$ cells such as NK cells, e.g., CD3$^-$ CD56$^+$ cells.

According to the monitoring methods provided herein, the level of Ki-67 expression in T-lymphocytes can be detected by flow cytometry of peripheral blood mononuclear cells (PBMCs) obtained from the cancer patient being treated with an OX40 agonist. In certain aspects, the PBMCs can be analyzed by flow cytometry for increased expression of Ki-67 in cells expressing of the CD3, CD95, and CD4 markers. In certain aspects, the PBMCs can be analyzed by flow cytometry for increased expression of Ki-67 in cells expressing of the CD3, CD95, and CD4 markers, and also the FoxP3 marker. In certain aspects, the PBMCs can be analyzed by flow cytometry for increased expression of Ki-67 in cells expressing of the CD3, CD95, and CD8 markers. In certain aspects, the PBMCs can be analyzed by flow cytometry for increased expression of Ki-67 in cells expressing of the CD3, CD95, and CD8 markers, and also the CD28 marker. In certain aspects, the PBMCs can be analyzed by flow cytometry for increased expression of Ki-67 in cells expressing of the CD3, CD95, and CD8 markers, and also the HLA-DR marker, the CD38 marker, or the CD38 and HLA-DR markers.

The practice of embodiments encompassed by the disclosure will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall 2003); Harlow and Lane (1988) Antibodies: A Laboratory Manual (Cold Spring Harbor Press); Dieffenbach and Dveksler (2003) PCR Primer (Cold Spring Harbor Press).

All of the references cited above, as well as all references cited herein, are incorporated herein by reference in their entireties.

The following examples are offered by way of illustration and not by way of limitation.

EXAMPLES

Example 1: Clinical Trial Protocol

This Example describes a phase 1 dose-escalation clinical trial in which advanced cancer patients were treated with a murine anti-OX40 monoclonal antibody (mAb). Patients with metastatic solid malignancies (e.g. prostate, renal, melanoma, gastrointestinal, ovarian, and lung cancer) refractory to conventional therapy were enrolled in a phase 1 dose-escalation clinical trial using the 9B12 murine agonistic anti-human OX40 mAb (see below). Individuals, at least 18 years old, with measurable or evaluable metastatic cancer not curable with standard surgery, chemotherapy or radiation were eligible for the trial. Other eligibility criteria included Eastern Cooperative Oncology Group (ECOG) performance status 0-2 (see: Oken, M. M, et al., *Am J Clin Oncol* 5:649-655, (1982), adequate hematologic, renal, cardiac and hepatic function, and the ability to comprehend and sign a written informed consent document. Major exclusion criteria were the presence of human anti-mouse antibodies (HAMA) before treatment, clinically significant autoimmune disease, HIV infection, serum positivity for hepatitis B or C, or allergy to tetanus or shellfish.

(a) Patients and Protocol

The demographics of the patents are presented in Table 1. Prior therapy for the enrolled patients included surgery, radiation, chemotherapy, targeted therapy and immunotherapy. All patients had performance status ECOG 0 or 1. The median number of prior cancer treatments was 2 (range 0-8) and all had progression of their cancer at the time of enrollment.

All patients received intravenous infusion of anti-OX40 mAb on days 1, 3 and 5 of a single cycle. Patients were enrolled sequentially in cohorts 1-3. Patients received 0.1 mg/kg of anti-OX40 mAb, 0.4 mg/kg and 2 mg/kg in cohorts 1, 2, and 3 respectively. Patients were randomly enrolled to receive two different sequences of reporter antigen injections. Arm A received KLH on day 1 and tetanus vaccine on day 29, while patients on arm B received tetanus vaccine on day 1 and KLH on day 29. Peripheral blood samples were collected either as a leukapheresis on days 0 and 57, or regular blood draws on days 5, 8, 15, 29, 36 and 43. In addition, 10 normal donors were given a tetanus toxoid vaccine on day 1 and had blood samples collected at the same time points as patients on the trial. The clinical trial was conducted solely at the Providence Portland Medical Center, Portland, Oreg., and was approved by the hospital's institutional review board. All patients and normal donors provided written informed consent.

(b) Blood Sample Collection, Preparation and Cryopreservation

Whole blood was collected in vacutainer tubes containing sodium heparin (BD vacutainer). Peripheral blood mononuclear cells were isolated from whole blood by density gradient centrifugation using Ficoll-Hypaque (Pharmacia). Cells recovered from the interface were washed twice in RPMI (Lonza) and frozen in 10% DMSO. Leukapheresis performed on days 0 and 57 was performed according to the standard procedures of the American Red Cross.

(c) Anti-OX40 mAb (9B12)

9B12 is a murine IgG1, anti-OX40 mAb directed against the extracellular domain of human OX40 (CD134) (Weinberg, A. D., et al. *J Immunother* 29, 575-585 (2006)). It was selected from a panel of anti-OX40 monoclonal antibodies because of its ability to elicit an agonist response for OX40 signaling, stability, and for its high level of production by the hybridoma. The 9B12 antibody was produced under good manufacturing practice conditions in a hollow fiber bioreactor and purified by protein-A chromatography. 9B12 mAb was equilibrated with phosphate buffered saline, pH 7.0, and its concentration was adjusted to 5.0 mg/ml by diafiltration, whereupon it was aliquoted into vials containing 3.3 ml each.

(d) Toxicity, Pharmacokinetics, and HAMA Assessment

Twenty-eight of 30 patients received all three planned anti-OX40 doses at the assigned dose level. Table 2 summarizes the toxicities related to anti-OX40. There was no correlation between the type or severity of toxicity with dose. Lymphopenia, fatigue, rash and flu-like symptoms with fever and chills were the most common toxicities; they usually started after the third anti-OX40 dose and generally resolved within 72 hours of the last dose. Two patients had episodic rashes and flu symptoms for up to 3 months after anti-OX40 that eventually resolved without steroids or immunosuppressive medications. The rashes were generally patchy, erythematous, and did not desquamate or blister.

Most toxicity was grade 1 or 2 with the exception of lymphopenia where grade 3 and 4 events were observed. The lymphopenia was transient (FIG. 1), with a mean nadir that didn't go below 0.7 cells$\times 10^6$ ml in cohorts 1 and 2 at day 8 and resolved by day 15 in cohort 1 and day 28 in cohort 2. Patients in cohort 3 did not develop lymphopenia. There were no adverse sequelae from lymphopenia. Seven patients developed asymptomatic splenomegaly by ultrasound, which was assessed because 40% of the non-human primates in the anti-OX40 toxicology study developed spenomegaly (Weinberg, A. D., et al. *J Immunother* 29, 575-585 (2006)). In general, the 9B12 anti-OX40 monoclonal antibody was well tolerated and the maximal tolerated dose (MTD) was not reached. Two patients died within four weeks of receiving the anti-OX40 monoclonal antibody, one from progressive metastatic lung cancer, and another from congestive heart failure, which was antecedent preexisting condition.

Anti-OX40 levels were determined in serum samples obtained from patients by ELISA according to the following method. Goat anti-human IgG, Fc gamma fragment antibody, (Jackson Labs), 2 µg/ml, was absorbed overnight at 4° C. onto the surface of 96-well plates (Fisher). Unbound capture antibody was washed off and a blocking solution of 1% Bovine Serum Albumin (Fisher) was added for 2 hrs at room temperature. CD134:Fc human ligand (Alexis), was added at 100 µl/well for 1 hr at room temperature. The 9B12 anti-OX40 monoclonal antibody (see above) was prepared at 200 ng/ml in 1% normal human serum and added to the plate as a positive control standard. Human serum samples were then added at an initial dilution of 1/100, and both the standard and test samples were serially diluted 2× down the rows. Following a 2-hr incubation at room temperature the plates were washed and peroxidase-linked sheep anti-mouse IgG, whole antibody, diluted 1:10,000 (GE, Amersham Biosciences) was added for 1 hour. Lastly, TMB substrate solution (Pierce TMB substrate kit) was added and allowed to incubate for 10 minutes in the dark. Immediately following, a stopping solution (2M $H_2SO_4$ solution) was added. Spectrophotometry measurements were made at 450 nm (Modulus Microplate, Turner Biosystems).

There was a dose-dependent increase in peak serum anti-OX40 levels as shown in FIG. 2. Anti-OX40 levels increased after the first and third dose (serum was not assessed following the second dose), and decreased thereafter. Peak anti-OX40 levels were observed 2 hours after the third dose (day 5), and a greater than 25-fold increase in peak anti-OX40 levels was observed comparing the lowest to the highest doses. The mouse-anti-OX40 monoclonal antibody was detected on the surface of PBMC when examined directly ex vivo by flow cytometry, using an anti-mouse specific antibody. Between 9.9 to 26.9% of CD4 T cells and 0.6 to 7.8% of CD8 T cells were positive using this technique (data not shown). These percentages were similar to what had been previously reported in the peripheral blood of humans using an OX40-specific antibody (Ma, B. Y., et al. *Blood* 106, 2002-2010 (2005)). All but one patient tested had high serum levels of HAMA on day 28 (data not shown). There was no increase in toxicity or HAMA titers as the dose increased.

Example 2: Tumor Response to Treatment

FIG. 3a shows a waterfall plot for best response by Response Evaluation Criteria in Solid Tumors (RECIST) criteria after anti-OX40 treatment. No patient achieved a partial response by RECIST criteria (>30% overall tumor shrinkage). However, at least one tumor nodule regressed in 12 patients and no change in the measurement of target lesions was observed in 6 individuals. The tumor types showing stability or regression were melanoma, renal, squamous of the urethra, prostate and cholangiocarcinoma. The longest interval of stability lasted 470 days in a patient with renal cancer, who received no other therapy during that time. Some individuals showed a decrease in disease at day 29, but progression on day 57. FIG. 3b-m show examples of tumor regression in three separate patients following anti-OX40 treatment, some of which measured greater than 2 cm in diameter. Mixed responses (e.g.: simultaneous regression of at least one tumor deposit and progression at other sites) were observed in two patients with melanoma and two patients with renal cancer.

The maximum tolerated dose (MTD) was not reached following one round of therapy with the dose levels tested. The majority of patients had failed all prior conventional therapy and had progressive disease prior to receiving anti-OX40. There was evidence of tumor shrinkage in 12/30 patients following one round of treatment. This included established metastatic lesions that were greater than 2 cm in diameter, which completely regressed (FIG. 3). Additional cycles of an OX40 agonist are expected to lead to increased immunologic activation and greater tumor regression.

Example 3: Antibody and T-Cell Responses to Reporter Antigens

Patients at all three dose levels were randomized into two groups; arm A patients received keyhole limpet hemocyanin (KLH) on day 1 following administration of the 9B12 anti-OX40 monoclonal antibody, followed by a tetanus vaccine on day 29, and arm B received tetanus on day 1 and KLH on day 29. Patients would likely have been naïve to KLH antigen, but tetanus would be a "recall" antigen. Antibody titers were assessed by ELISA according to the following method. Recombinant Tetanus Toxin C fragment, (Roche), at 2 µg/ml, was absorbed overnight at 4° C. onto the surface of 96-well plates (Fisher). Unbound antigen was washed off and a blocking solution of 5% bovine serum albumin (Fisher) was added. Patient and normal donor serum dilutions were then added at an initial dilution of 1/50 and serial 3× dilutions were done down the rows. After 1-hour at room temperature the plates were washed and peroxidase-conjugated goat anti-human IgG, diluted 1:100,000 (Jackson Immuno Research Lab) was added for 1 hour. Lastly, TMB substrate solution (SureBlue TMB, KPL Inc) was added and allowed to incubate for 10 minutes in the dark followed by a stopping solution (85% O-Phosphoric Acid, Fisher). Spectrophotmetry measurements were made at 450 nm (Wallac Victor2 spectrophotometer, Perkin Elmer).

KLH (Biosyn Corp), at 10 µg/ml, was absorbed overnight at 4° C. onto the surface of 96 well flat bottom maxisorb plates. The same protocol employed in the tetanus ELISA was used except that human serum samples were added at an initial 1/25 dilution, followed by serial 2× dilutions down the rows.

For all statistical tests of serum antibody responses to KLH and tetanus, a cut-off optical density (OD) value was established that would determine the dilution at which the sera would be considered negative (endpoint dilution). A best-fit curve generated by a 1-phase Decay model was used to determine the OD values for the bottom plateau for each ELISA plate. The mean for all of the plateaus on the plate+4 standard deviations was used as the cut-off OD. The dilution at which each curve intersected the cutoff is the endpoint dilution (titer) for that curve. The two arms from all three cohorts were compared using a two-tailed Mann-Whitney (Wilcoxon rank-sum test) analysis to determine whether the mean fold-change increased significantly from baseline between the two arms.

Antibody levels to KLH and tetanus were assessed 15 days after immunization (peak of the antibody response), which was either on day 15 or 43 for Arm A and Arm B, respectively, after administration of the 9B12 anti-OX40 monoclonal antibody. Anti-tetanus antibody titers were calculated both pre- and post-anti-OX40 administration and fold-increases were calculated for all patients. A significant fold-increase was found in patients that were immunized with tetanus on the same day as anti-OX40 administration (Arm B) as compared to patients immunized 28 days later (Arm A) (p=0.0158) (FIG. 4a).

T cell proliferation in response to tetanus toxoid was examined by the following method. Cryopreserved PBMC from indicated time points for each patient were thawed and $1 \times 10^5$ PBMC per well (96 well plate) in triplicate were incubated in X-VIVO15 (Lonza) containing 5% pooled normal human serum. Cells were stimulated with a costimulatory antibody cocktail, anti-CD28/anti-CD49d (BD Biosciences), at 0.5 µg/ml, and with tetanus toxoid antigen (EMD Calbiochem) at 1 ug/ml for 4 days. On day 4 cells were labeled with 4 uCi/ml of [$^3$H]Thymidine (MP Biomedicals) for 18 hrs before they were collected on filter pads and counted on a Wallac Trilux Microbeta scintillation counter. A two-tailed unpaired t-test was used to determine whether the mean thymidine incorporation was significantly increased when comparing the pre-treatment levels to either day 43 for Arm A or day 15 for Arm B.

Tetanus-specific T cell proliferation from PBMCs obtained pre- and 15-post immunization was also assessed as above, and was similar to the antibody response there was a significant increase in proliferation in the post-anti-OX40 samples associated with Arm B, but not in Arm A (FIG. 4b). Antibody levels to KLH were also assessed in a similar fashion to tetanus. Patients receiving anti-OX40 on the same day they were immunized with KLH (Arm A) had a significant fold increase in KLH antibody titers compared to patients receiving KLH 28 days after anti-OX40 monoclonal antibody administration (Arm B) (FIG. 4c, p=0.007).

In summary, anti-OX40 treatment significantly increased antibody titers and T cell recall responses to tetanus immunization (FIG. 4a-b). There are currently several clinical trials that are immunizing cancer patients with tumor antigens, and this observation increases the rationale for using anti-OX40 to increase T and B cell responses to immunization Ag in future clinical studies.

Example 4: T-Lymphocyte Profiling and Proliferation

To determine the effects of anti-OX40 on peripheral T lymphocytes, a 10-color flow cytometry assay was developed using labeled antibodies that recognized the following surface and intra-cellular proteins: CD3, CD4, CD8, CD95, CD25, FoxP3, CD28, CCR7, CD127, and Ki-67. Flow cytometry was carried out by the following method. PBMC were obtained from patients at specific times as noted in Example 1, and the cryopreserved samples were used for flow cytometry studies. The fluorochrome-labeled antibodies to CD3 (SK7), CD4 (SK3), CD8 (RPA-T8), CD95 (DX2), HLA-DR (L243), CCR7 (3D12), and Ki-67 (B56) were purchased from BD Pharmingen, CD127 (eBioRDR5) and Foxp3 (236A/E7) from eBioscience, CD28 (CD28.2) from Beckman Coulter, CD25 (4E3) from Miltenyi Biotech and CD38 (HIT2), CD8 (3B5) and Streptavidin AF-700 from Invitrogen. Intracellular staining was performed using the Fix/Perm kit from eBioscience according to the manufacturer's instructions. To prevent the interference of HAMA with staining, cells were preincubated with the 9B12 anti-OX40 monoclonal antibody. Detection of anti-OX40 binding was performed on fresh PBMC using an anti-mouse IgG and FITC-labeled anti-rat IgG (Invitrogen). Stained cells were analyzed on an LSRII or the FACS Aria (BD Biosciences). Data analysis was performed using either Winlist (Verity Software House) or FACSDiva (Becton Dickinson) software. Statistical analysis of Ki-67 expression was carried out as follows. For each cell population, mean differences between treatment cohorts at study days 8 and 15 were compared using one-way analysis of variance (ANOVA) on the $\log_{10}$ fold-change from baseline. The $\log_{10}$ transformation was performed to satisfy statistical model assumptions. Comparisons between cohorts were not adjusted for multiple comparisons due to the exploratory nature of the analyses. Mean differences in fold-change between responders and non-responders (see Example 5 below) at each study day were analyzed using one-way ANOVA. Analyses were performed using JMP version 9 (SAS Institute).

Ki-67 expression, a marker present only within proliferating cells, was examined, since OX40 agonists are known to increase T cell proliferation. The phenotypic changes in CD4$^+$ and CD8$^+$ T cells from two representative patients (from cohorts 1 and 2) after anti-OX40 administration, and from a normal individual immunized with tetanus were analyzed directly ex vivo at several time points after antibody administration (FIG. 5a-b). Peripheral blood mononuclear cells (PBMC) were gated on CD3, CD95, and CD4, markers reported to identify Ag-experienced/memory T cells (Pitcher, C. J., et al. *J Immunol* 168, 29-43 (2002)), and further analyzed for FoxP3 (Tregs) and Ki-67 (FIG. 5a). PBMC from the same patients were also gated on CD3, CD95, and CD8 and analyzed for CD28 and Ki-67 (FIG. 5b). At baseline the percentage of proliferating/Ki-67$^+$ CD4+ and CD8$^+$ T cells ranged between 0.5-6.0% in patients and normal controls (FIG. 5 and data not shown). The percentage of Ki-67$^+$ CDR4$^+$ T cells started to increase early (day 8) and the Ki-67$^+$ CD8$^+$ T cells later (day 15) after anti-OX40 monoclonal antibody administration (summarized in FIG. 6); the percentage of proliferating cells in both populations usually returned to pre-anti-OX40 mAb administration percentages by day 57. Typically, proliferating CD8$^+$ T cells were observed in both the CD28 positive and negative populations on day 15; however, the majority of proliferating CD8$^+$ T cells on day 29 were CD28$^+$. Anti-OX40 treatment also increased the proliferation of CD3$^-$ CD56 cells (most likely NK cells, FIG. 6d). No significant changes in the percentage of Ki-67$^+$ PBL were detected among the normal donors that were immunized with tetanus toxoid for any of these populations at any time points (FIG. 6).

The mean fold-increase of Ki-67$^+$ lymphocytes among PBL sub-populations are summarized in FIG. 6 for all three cohorts and the controls. There was a significant increase in Ki-67$^+$ (proliferating) lymphocytes in anti-OX40 antibody-treated patients compared to the control group. Significant changes were observed for CD4$^+$/FoxP3$^{neg}$ T cells (FIG. 6a), CD8$^+$ T cells (FIG. 6c) and CD3$^-$/NK cells (FIG. 6d). The proliferation of the CD4$^+$ FoxP3$^{pos}$ Tregs was unaffected in anti-OX40 treated patients at any dose or in the control group (FIG. 6b). At day 15, the proliferation of CD4$^+$ FoxP3$^{neg}$ cells showed a statistically significant increase in cohorts 1 and 2 compared to the control group (p<0.02). The augmentation of CD4$^+$ FoxP3$^{neg}$ T cell proliferation in patients within the third cohort peaked on day 8 and declined thereafter, which was a different pattern of expression that the first two cohorts. The increase in proliferation of CD8$^+$ T cells peaked on day 15 for all three cohorts; however, a significant increase in proliferation was only observed in the second cohort when compared to the control group (p=0.001). A sustained increase in Ki-67$^+$ CD8$^+$ T cells was found only in patients from the second cohort (out to day 29). The average increase in proliferation of the CD8$^+$ T cells in cohort 3 was quite a bit less than that observed in cohort 2, despite the fact that patients received a five-fold higher dose of the anti-OX40 monoclonal antibody. The increase in Ki-67 expression within the CD3$^7$/CD56$^+$ cells was statistically significant in all cohorts compared to normal donors and peaked 15 days after anti-OX40 monoclonal antibody treatment. Overall, the largest average fold-increase in the percentage of cycling cells for all three cell populations (CD4$^+$/FoxP3$^{neg}$, CD8$^+$, and NK cells) was observed in cohort 2 (FIG. 6).

A significant increase in proliferation of both CD4$^+$ and CD8$^+$ T cells was observed starting seven days after the initial infusion and lasting for at least 15 days, and sometimes up to a month. Three doses of anti-OX40 monoclonal antibody were tested and there were some dose-related immunologic effects. There was a dose-dependent increase in CD4$^+$ and CD8$^+$ T cell proliferation when the dose was increased from 0.1 to 0.4 mg/kg. However, at the highest dose (2 mg/kg), a different kinetic pattern of CD4+ T cell proliferation as well as a reduced increase in CD8+ T cell proliferation was observed. Anti-OX40 did not appear to increase Treg cell proliferation (CD4+/FoxP3$^{pos}$) at any dose suggesting that OX40 agonists preferentially drove proliferation of effector T cells in cancer patients. This pattern of immunologic response could be of benefit to cancer patients, because Treg cells are known to dampen immunity to tumor cells (Colombo, M. P. & Piconese, S. *Nat Rev Cancer* 7, 880-887 (2007)). Ki-67 expression by T cells has also recently been assessed in prostate cancer patients treated with anti-CTLA-4 (Kavanagh, B., et al. *Blood* 112, 1175-1183 (2008)). Anti-CTLA-4 increased proliferation of both FoxP3$^{pos}$ and FoxP3$^{neg}$ CD4+ T cells in a dose-dependent manner (Id.). There was no assessment of CD8+ T cell proliferation or any correlation of Ki-67 increases with clinical responses within this publication.

Since all patients mounted a HAMA response to the murine anti-OX40 monoclonal antibody the possibility existed that the increase in Ki-67+ cells could be attributed to an anti-mouse specific immune response or tetanus immunization rather than enhancing the endogenous T cell repertoire. Since this could not be directly tested in humans, a study was performed in non-human primates to determine whether the infusion of a control mouse IgG protein in combination with a tetanus vaccine would elicit a similar increase in Ki-67+ expression by CD4+ and CD8+ T cells as was observed in the clinical trial (see FIG. 6). The following methods were used. Eight female rhesus macaques (*Macaca mulatta*) born and reared at the Oregon National Primate Research Center (ONPRC) were divided into two groups (4 monkeys/group). Group 1 was given the 9B12 anti-OX40 monoclonal antibody and Group 2 was given a control mouse IgG1 (MOPC-21), both at 1.0 mg/kg by intravenous infusion on days 1, 3 and 5. All monkeys each also received a tetanus toxoid vaccine on day 1 prior to mAb infusion. Blood samples were obtained on days 1, 7, 14, 21, 28 and 35 and PBMC were analyzed using a multi-parameter flow analysis panel as described above.

PBMC were analyzed by flow cytometry with a panel similar to the one described earlier for human PBL. The mouse anti-human OX40 antibody increased Ki-67 expression of both CD4+ and CD8+ T cells over time (FIG. 7). No significant increases in Ki-67 expression were observed in either CD4+ or CD8+ lymphocytes isolated from monkeys that had received tetanus and mouse IgG. These data show that increased Ki-67 expression was induced by specific engagement of OX40 and not by a de novo immune response elicited to a foreign mouse protein or tetanus immunization.

Example 5: Correlation of T Lymphocyte Proliferation and Delayed Cancer Progression A summary of the clinical response for patients in this phase I trial are detailed in FIG. 3A. Three patterns of clinical response were detected after one cycle of anti-OX40 monoclonal antibody treatment: 1) evidence of initial shrinkage of tumor, 2) no change in tumor burden during the two month evaluation, and 3) progression/tumor growth. In a post-hoc analysis patients were grouped into two categories: 1) patients who had an initial decrease in their tumor mass or stabilization of their disease ("non-progressor" group, (n=19)), and 2) patients whose tumors progressed ("progressor" group (n=10)). Using flow cytometry as described in Example 4, Ki-67 expression was compared following anti-OX40 treatment between the progressor and non-progressor groups. The fold-increase in Ki-67+ T cells among the CD4+/FoxP3$^{neg}$ population in the non-progressor group on day 8 following administration of the anti-OX40 monoclonal antibody was significantly greater compared to the increase among the progressor group, 2.7-fold versus 1.6-fold with p<0.05 (FIG. 8a). The increased expression of Ki-67 among CD8+ T lymphocytes in the non-progressor group was also significantly greater on days 5, 8 and 15 when compared to the progressor group (p≤0.01) (FIG. 8b). No significant differences were observed when the progressor and non-progressor groups were assessed for Ki-67 expression in CD4+ Foxp3$^{pos}$ T cells or CD3− lymphocytes (FIG. 8c-d). These results suggest that the proliferative response within the CD4 effector sub-population followed by CD8+ T cell proliferation correlates with a delayed progression of cancer in patients treated with anti-OX40 monoclonal antibody.

Example 6: Anti-OX40 Administration Induces Qualitative Changes in Cycling CD8+ T Cells The effect of anti-OX40 on the activation phenotype of cycling CD8+ T cells was examined by assessing co-expression of CD38 and HLA-DR, which is a hallmark of proliferating, viral-specific human CD8+ T cells following vaccination (Miller, J. D., et al. *Immunity* 28, 710-722 (2008)). The expression of CD38 and HLA-DR on CD8+/Ki-67+ T cells at different times after anti-OX40 administration was analyzed, using the flow cytometry methods described in Example 4. FIG. 9a shows an individual patient in whom 1.3% of the CD8+ T cells were Ki-67+ and 64.2% of them co-expressed CD38 and HLA-DR prior to treatment. The percentage of Ki-67 positive CD8+ T cells increased to 16.3 and 20.3% on day 15 and 29 respectively, and on day 29 greater than 95% of the cycling cells were highly positive for both CD38 and HLA-DR (FIG. 9a). There was still a higher percentage of cells expressing both activation markers on the cycling CD8+ T cells two months after anti-OX40 infusion even though the percentage of CD8+/Ki-67+ cells had returned to base-line levels. The mean percentage of CD38+/HLA-DR+/Ki-67+ CD8+ T cells in eleven anti-OX40 treated patients (patients analyzed from all three cohorts) was compared with nine normal donors immunized with tetanus (FIG. 9b). At Days 29 and 57, there was a statistically significant increase in the percentage of HLA-DR+/CD38+ proliferating CD8+ T cells when compared to controls, suggesting that engagement of OX40 not only increased proliferation of CD8+ T cells, but also increased their activation phenotype.

The increase in activated CD8+ T cell phenotype shows that treatment with anti-OX40 monoclonal antibody can increase the immunologic potency of these cells. As shown in Example 7 below and FIG. 10, tumor-specific proliferating (Ki-67+) T cells increased following anti-OX40 monoclonal antibody treatment.

Example 7: Tumor-Specific Immune Responses

Anti-OX40 elicited immune activation as assessed by augmentation of responses to a neoantigen (KLH), a recall antigen (tetanus), and proliferation of peripheral blood T cells with effector and memory phenotypes (Example 3). In addition, tumor-specific immune responses following administration of anti-OX40 monoclonal antibody were measured by the following method. Tumor-specific reactivity before and after anti-OX40 monoclonal antibody administration was assessed in PBMC from 3 melanoma patients for whom autologous and HLA-non-matched tumor cell lines were available. Autologous or HLA-matched melanoma cells were co-cultured with PBMC from the pheresis product obtained prior to or 57 days post-treatment, at a PBMC:tumor ratio of 8:1 for five days. Supernatants were harvested and IFN-γ secretion was quantified using an IFN-γ ELISA kit (BD Biosciences). INFγ secretion from supernatants containing either pre-treatment or post-treatment PBMC co-cultured with either autologous, HLA-mismatched cell line, or Flu, were compared using a one-tailed unpaired t-test to determine if the change was significant.

Significant increases in IFN-γ were found in the PBMC/tumor supernatants post-anti-OX40 treatment in 2 out of 3 patients (FIG. 10a-b). IFN-γ levels were increased in response to autologous tumor cells in two patients, but not in response to HLA-mismatched tumor lines, and these increases were primarily elicited by CD8 T cells (data not shown). In these samples there were no significant differences in influenza-induced IFN-γ production by PBMC collected before or after anti-OX40 monoclonal antibody administration.

Anti-OX40 monoclonal antibody has previously been shown to enhance antibody production (Evans, D E et al., *J. Immunol* 167:6804-6801 (2001)). Accordingly, the presence of tumor-specific antibodies was measured before and after anti-OX40 monoclonal antibody treatment. Serum from a melanoma patient was used to probe protein lysates from a melanoma cell line (Femex) and an embryonic kidney cell line (HEK293) by Western blot before and after anti-OX40 treatment (days 0, 8, 15, 29, 36). The arrow in FIG. 9c follows a 27 kd band that is present in the melanoma lysate lanes and increases in intensity over time after anti-OX40 administration, but is absent in kidney lysate lanes. The 27 kd band was also detected in two other melanoma cells lines with the day 15 sera from this patient (data not shown). Hence, it appears that anti-OX40 treatment increased this patient's production of tumor specific antibodies at least to one antigen.

Experiments will be carried out to show that both endogenous and tumor vaccine specific immune responses are increased if an OX40 agonist was combined with a tumor vaccine.

The foregoing disclosure is sufficient to allow others, by applying knowledge within the skill of the art, to readily modify and/or adapt the disclosure for various related applications without undue experimentation. Therefore, such adaptations and modifications are intended to be within the meaning and range of equivalents of the disclosure, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the this disclosure should not be limited by any of the above-described exemplary embodiments, but should be defined only in accordance with the following claims and their equivalents.

TABLE 1

Patients Characteristics

|  | Number (percent or range) |
|---|---|
| Male/Female | 24/6 (80/20) |
| Median Age | 60 (range 36-80) |

TABLE 1-continued

Patients Characteristics

|  | Number (percent or range) |
|---|---|
| ECOG |  |
| 0 | 23 (77) |
| 1 | 7 (23) |
| Tumor Primary Site |  |
| Melanoma | 7 (23) |
| GI | 7 (23) |
| Renal | 5 (17) |
| Prostate | 5 (17) |
| Lung | 3 (10) |
| Other | 3 (10) |
| Sites of Metastases |  |
| Lymph Node | 15 (50) |
| Lung | 12 (40) |
| Liver | 10 (33) |
| Bone | 7 (23) |
| Other | 14 (47) |
| Median number of metastatic sites | 2 (range 1-4) |
| Surgery | 21 (70) |
| Radiation | 14 (47) |
| Chemotherapy | 19 (63) |
| Immunotherapy | 13 (43) |
| Targeted Agents | 9 (30) |
| Hormonal Therapy | 5 (17) |

TABLE 2

Adverse Events

| Toxicity | Grade 1 | Grade 2 | Grade 3 | Grade 4 |
|---|---|---|---|---|
| Lymphopenia | 3 | 10 | 6 | 1 |
| Fatigue | 7 | 12 |  |  |
| Rash/Skin Changes | 4 | 6 |  |  |
| Pruritis | 5 | 1 |  |  |
| Fever/Chills | 11 | 2 |  |  |
| Splenomegaly | 7 |  |  |  |
| Arthralgias/Myalgias | 5 | 5 |  |  |
| Nausea/Vomiting | 4 | 3 |  |  |
| Increased AST, ALT or alkaline phosphatase | 2 | 1 |  |  |
| Anemia | 1 | 8 |  |  |

What is claimed is:

1. A method of treating cancer, comprising
   a. administering to a patient in need of treatment an effective amount of an anti-OX40 antibody or antigen-binding fragment thereof,
   b. detecting the level of Ki-67 expression in the patient's CD8$^+$ T-lymphocytes and CD4$^+$/Foxp3$^-$ T-lymphocytes obtained at one or more time points following the administration of the anti-OX40 antibody or antigen-binding fragment thereof, for an increase in the level of Ki-67 expression compared to a corresponding baseline level of Ki-67 expression,
   c. identifying the patient as a progressor where Ki-67 expression is not increased compared to a corresponding baseline expression, and
   d. administering an adjusted or additional effective amount of anti-OX40 antibody or antigen-binding fragment thereof to the progressor patient,
   wherein the administration of anti-OX40 antibody or antigen-binding fragment thereof can stimulate CD8$^+$ T-lymphocyte or CD4$^+$/Foxp3$^-$ T-lymphocyte activity against cancer cells in the patient.

2. The method of claim 1, wherein the corresponding baseline level of Ki-67 expression is established by averaging the Ki-67 expression level in CD8$^+$ T-lymphocytes and CD4$^+$/Foxp3$^-$ T-lymphocytes obtained from a population of donors.

3. The method of claim 1, wherein the corresponding baseline level of Ki-67 expression is the Ki-67 expression level in CD8+ T-lymphocytes and CD4$^+$/Foxp3$^-$ T-lymphocytes obtained from the patient prior to administration of the anti-OX40 antibody or antigen-binding fragment thereof.

4. The method of claim 1, further comprising monitoring for an increase in the proportion of CD8$^+$ T-lymphocytes expressing CD38, HLA-DR expression, or both CD38 and HLA-DR compared to a corresponding baseline level of CD8$^+$ T-lymphocytes expressing CD38, HLA-DR expression, or both CD38 and HLA-DR.

5. The method of claim 1, wherein an increase in the level of Ki-67 expression is detected in a tumor-specific subpopulation of CD8$^+$ T-lymphocytes and CD4$^+$/Foxp3$^-$ T-lymphocytes.

6. The method of claim 1, wherein an increase in the level of Ki-67 expression is detected in memory CD8$^+$ T-lymphocytes.

7. The method of claim 1, wherein the antibody or antigen-binding fragment thereof binds to the same OX40 epitope as mAb 9B12.

8. The method of claim 1, wherein the level of Ki-67 expression in CD8$^+$ T-lymphocytes is detected by flow cytometry of peripheral blood mononuclear cells (PBMCs) for expression of CD3, CD95, and CD8 markers.

9. The method of claim 1, wherein the antibody or antigen binding fragment thereof is a monoclonal antibody.

10. The method of claim 9, wherein the antibody or antigen binding fragment thereof is a chimeric antibody.

11. The method of claim 9, wherein the antibody or antigen binding fragment thereof is a humanized antibody.

12. The method of claim 1, wherein the antibody or antigen binding fragment thereof is a human antibody.

13. The method of claim 1, wherein the antigen-binding fragment is an Fab fragment.

14. The method of claim 1, wherein the antigen-binding fragment is an Fab' fragment.

15. The method of claim 1, wherein the antigen-binding fragment is an F(ab)2 fragment.

16. The method of claim 1, wherein the antigen-binding fragment is a single-chain Fv fragment.

17. The method of claim 1, wherein the antigen-binding fragment is a single chain antibody.

18. The method of claim 1, further comprising administering to the patient at least one additional cancer treatment.

19. The method of claim 18, wherein said at least one additional cancer treatment is surgery, radiation, chemotherapy, immunotherapy, targeting anti-cancer therapy, hormone therapy, or any combination thereof.

* * * * *